United States Patent
Lee et al.

(10) Patent No.: US 11,191,808 B2
(45) Date of Patent: Dec. 7, 2021

(54) PHARMACEUTICAL COMPOSITION FOR SUPPRESSING CELL TRANSPLANT REJECTION

(71) Applicant: INDUSTRY-UNIVERSITY COOPERATION FOUNDATION HANYANG UNIVERSITY, Seoul (KR)

(72) Inventors: Dong Yun Lee, Seoul (KR); Yong Hwa Hwang, Seoul (KR); Min Hyung Lee, Gyeonggi-do (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 1331 days.

(21) Appl. No.: 15/323,377

(22) PCT Filed: May 18, 2015

(86) PCT No.: PCT/KR2015/004936
§ 371 (c)(1),
(2) Date: Apr. 24, 2017

(87) PCT Pub. No.: WO2016/003067
PCT Pub. Date: Jan. 7, 2016

(65) Prior Publication Data
US 2017/0224769 A1      Aug. 10, 2017

(30) Foreign Application Priority Data
Jul. 4, 2014   (KR) .................. 10-2014-0083648

(51) Int. Cl.
A61K 38/17     (2006.01)
A61K 35/39     (2015.01)
A61K 38/16     (2006.01)
C12N 7/00      (2006.01)

(52) U.S. Cl.
CPC .......... *A61K 38/1709* (2013.01); *A61K 35/39* (2013.01); *A61K 38/162* (2013.01); *C12N 7/00* (2013.01); *C07K 2319/10* (2013.01); *C12N 2740/16311* (2013.01); *C12N 2740/16322* (2013.01); *C12N 2740/16371* (2013.01)

(58) Field of Classification Search
None
See application file for complete search history.

(56) References Cited

U.S. PATENT DOCUMENTS

2004/0156851 A1 *  8/2004  Newman ............ C07K 14/4702
                                                   424/145.1
2008/0075728 A1 *  3/2008  Newman ................ A61P 17/06
                                                   424/152.1
2009/0148453 A1 *  6/2009  Newman ............... A61K 39/395
                                                   424/139.1
2010/0173277 A1 *  7/2010  Yasunami ................ A01N 1/02
                                                      435/1.1
2013/0183348 A1    7/2013  Taniguchi et al.

OTHER PUBLICATIONS

Matsuoka, High-mobility group box 1 is involved in the initial events of early loss of transplanted islets in mice, The Journal of Clinical Investigation, vol. 120 No. 3 Mar. 2010 (Year: 2010).*
Zhang, HMGB1, an innate alarmin, in the pathogenesis of type 1 diabetes, Int J Clin Exp Pathol 2010;3(1):24-38 (Year: 2010).*
Kruger et al., Islet-expressed TLR2 and TLR4 sense injury and mediate early graft failure after transplantation, Eur J Immunol. Oct. 2010 ; 40(10): 2914-2924. (Year: 2010).*
Serwer et al., Systemic and Local Drug Delivery for Treating Diseases of the Central Nervous System in Rodent Models. J. Vis. Exp. (42), e1992, 2010. (Year: 2010).*
Kim'JDT, Combination of TAT-HMGB1A and R3V6 amphiphilic peptide for plasmid DNA delivery with anti-inflammatory effect, Journal of Drug Targeting, 22:8, 739-747, May 15, 2014 (Year: 2014).*
Kokkola et al., Successful Treatment of Collagen-Induced Arthritis in Mice and Rats by Targeting Extracellular High Mobility Group Box Chromosomal Protein 1 Activity, Arthiritis & Rheumatism, vol. 48, No. 7, Jul. 2003, pp. 2052-2058 (Year: 2003).*
AFPS 2013 Conference brochure, The Asian Federation for Pharmaceutical Sciences Conference 2013 (AFPS 2013) in Jeju, Republic of Korea.
Final Program CTS 2013 12$^{th}$ Congress of the Cell Transplant Society, Milan, Italy, Jul. 7-11, 2013. www.ets2013.org, p. 52.
Huang et al., Extracellular Hmgb1 Functions as an Innate Immune-Mediator Implicated in Murine Cardiac Allograft Acute Rejection, American Journal of Transplantation 2007; 7:799-808.
HwaHwnag et at., "Cytoprotection of xenotransplanted pancreatic islets using cellular delivery of tat-high mobility group box 1a fusion protein", AFPS 2013 Proceedings, p. 195, Asian Federation of Pharmaceutical Sciences Conferences, Advances in Pharmaceutical Sciences-Next Generation, Nov. 20, 2013, Ramada Plaza Jeje Hotel, Jeju Republic of Korea.
Itoh et al., "Elevation of High-Mobility Group Box 1 After Clinical Autologous Islet Transplantation and Its Inverse Correlation With Outcomes", Cell Transplantation, vol. 23, pp. 153-165, 2014.
Kim et al., "Combination of TAT-HMGB1A and R3V6 amphiphilic peptide for plasmid DNA delivery with anti-inflammatory effect", Journal of Drug Targeting, 2014; 22(8): 739-747.
Kim et al., "Expression, purification and characterization of TAT-high mobility group box-1A peptide as a carrier of nucleic acids", Biotechnol Letters (2008) 30:1331-1337.

* cited by examiner

Primary Examiner — Louise W Humphrey
Assistant Examiner — Srikanth Patury
(74) Attorney, Agent, or Firm — Adsero IP

(57) ABSTRACT

The present invention relates to a pharmaceutical composition for inhibiting rejection of transplanted cells including a high mobility group box 1 A domain (HMGB1A) as an active ingredient. The use of the pharmaceutical composition can minimize immunological rejection, which may occur upon cell transplantation, and increase the success rate of cell transplantation.

6 Claims, 29 Drawing Sheets
Specification includes a Sequence Listing.

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Arg Lys Lys Lys Arg Arg Gln Arg Arg Arg
1               5                   10

<210> SEQ ID NO 2
<211> LENGTH: 30
<212> TYPE: DNA
<213> ORGANISM: Artificial Sequence
<220> FEATURE:
<223> OTHER INFORMATION: Synthetic construct
```

```
<400> SEQUENCE: 2
ccggaattca tgggcaaagg agatcctaag                                  30

<210> SEQ ID NO 3
<211> LENGTH: 33
<212> TYPE: DNA
<213> ORGANISM: Artificial Sequence
<220> FEATURE:
<223> OTHER INFORMATION: Synthetic construct

<400> SEQUENCE: 3
cccaagcttg atgtaggttt tcatttctct ttc                              33

<210> SEQ ID NO 4
<211> LENGTH: 39
<212> TYPE: DNA
<213> ORGANISM: Artificial Sequence
<220> FEATURE:
<223> OTHER INFORMATION: Synthetic construct

<400> SEQUENCE: 4
gatccaagct tcgcaaaaag cggagacaga gacgcaggg                        39

<210> SEQ ID NO 5
<211> LENGTH: 39
<212> TYPE: DNA
<213> ORGANISM: Artificial Sequence
<220> FEATURE:
<223> OTHER INFORMATION: Synthetic construct

<400> SEQUENCE: 5
aattccctgc gtctctgtct ccgctttttg cgaagcttg                        39
```

PHARMACEUTICAL COMPOSITION FOR SUPPRESSING CELL TRANSPLANT REJECTION

TECHNICAL FIELD

The present invention was supported by a grant from the Korean Ministry of Education (Grant No. 201400000001005). The specialized agency of R&D management with regard to the grant number, 201400000001005, is the National Research Foundation of Korea, the research program title is "Basic Research Project in Science and Engineering/Research Project for Senior Researchers/Acceleration Research", the research project title is "Study of Cell Medicine for Regulating immune Response using Nanohybrid. System", the lead agency is the Industry-Academic Cooperation Foundation of Hanyang University, and the project period is May 1, 2014 to Apr. 30, 2015.

This application claims priority to and is a 35 U.S.C. §371 national phase application of PCT/KR2015/004936 (WO2016/003067), filed on May 18, 2015 entitled "PHARMACEUTICAL COMPOSITION FOR SUPPRESSING CELL TRANSPLANT REJECTION", which application claims priority to and the benefit of Korean Patent Application No. 10-2014-0083648, filed Jul. 4, 2014; the disclosures of which is incorporated herein by reference in their entirety.

Incorporated by reference herein in its entirety is the Sequence Listing entitled "0338_114PCT-US_ST25" created Aug. 3, 2021, size of 1.21 kilobytes.

The present invention relates to a pharmaceutical composition for inhibiting rejection of transplanted cells.

BACKGROUND ART

Important issues in a treatment process using a cell therapy product in vivo are (1) immune responses to the administered cell therapy product and (2) non-specific inflammatory responses caused by the surrounding environment at the site of administration. These important problems result in early graft loss in which 60 to 80% of in vivo administered cell therapy products fail to function. The main molecular mechanism explaining these problems is as follows: when a cell therapy product suffers minor damage, a high mobility group box 1 protein (HMGB1: a type of transcription factor) is released from cells in the cell therapy product, and the released HMGB1 binds to receptors such as TLR2/4 and RAGE, which are present in the cell membranes of cells such as surrounding immune cells, to induce immune responses and inflammatory responses. Eventually, when this process is sustained, the cell therapy product ceases to function.

For example, in the case of pancreatic islet transplantation for the treatment of diabetes, an excessive amount of HMGB1 is released from pancreatic islet cells due to surgical injuries at the beginning of surgery and immune responses, and consequently the released HMGB1 induces additional interactions between the transplanted pancreatic islet cells and other immune cells, whereby serious immune responses occur. Eventually, most of the transplanted pancreatic islet cells are destroyed and lose their ability to secrete insulin, resulting in a failure to treat diabetes. Accordingly, as can be seen from the above example, it is understandable that the development of technologies to regulate the release of HMGB1 protein in cells is very important.

Several studies have been conducted to inhibit the action of HMGB1, which is produced early in transplantation of pancreatic islet cells. For example, there are research results showing that antibodies specific to HMGB1, which are administered intravenously to cell-transplanted animals, reduce HMGB1-mediated immune responses (see Ulloa L, Messmer D. High-Mobility Group Box 1 (HMGB1) Protein: Friend and Foe. Cytokine Growth F R 17, 189-201 (2006), Huang Y, et al. Extracellular HMGB1 Functions as an Innate Immune-Mediator Implicated in Murine Cardiac Allograft Acute Rejection. Am J Transplant 7, 799-808 (2007)). In addition, it was demonstrated that, when performing an allograft, the level of blood glucose can be sufficiently controlled by transplanting a small number of cells under conditions of inhibiting the action of HMGB1. In addition, another study has shown that, when the high mobility group box 1 A domain (HMGB1A) is intraperitoneally or intravenously injected in a sepsis model, the HMGB1A has an effect of reducing secretion of immune substances as much as the HMGB1 antibodies (see Yang H, et al. Reversing Established Sepsis with Antagonists of Endogenous High-Mobility Group Box 1. Proc Natl Acad Sci USA 101, 296-301 (2004)). In addition, research results have shown that, when pancreatic islet cells are transplanted into the liver, administration of DHMEQ, which inhibits the transcription factor NF-κB, or antithrombin III, an anticoagulant, reduces the expression of HMGB1 in animals subjected to the allograft. In addition, studies are under way to demonstrate that the use of HMGB1 antibodies or siRNA inhibits the activity of HMGB1 and consequently inhibits angiogenesis in cancers.

Administration of additional drugs to reduce the level of HMGB1 after transplanting pancreatic islet cells is troublesome, and such administration may cause the patient pain. In addition, since most of the drugs do not target the transplanted cells but spread to the whole body, there is a limit in immediately obtaining the effect of the drugs, and administration of the drugs to the body may cause safety problems in subsequent clinical application. In addition, it is known that most technologies are effective only in an allograft, and other treatments are needed to improve the effects of the technologies when performing a xenograft.

Numerous papers and patent documents are referenced and cited throughout this specification. The disclosures of the cited papers and patent documents are incorporated herein by reference in their entirely to clearly understand the background of the art to which the present invention pertains and the content of the present invention.

DISCLOSURE

Technical Problem

The present inventors have tried to develop a method of minimizing immunological rejection that may occur upon cell transplantation for cell therapies and increasing the success rate of cell transplantation. As a result, the inventors have completed the present invention by confirming that the use of the high mobility group box 1 A domain (HMGB1 A), especially HMGB1A combined with a protein transduction domain (PTD), dramatically alleviates immunological rejection upon cell transplantation and increases the engraftment rate of transplanted cells.

Accordingly, the present invention is directed to providing a pharmaceutical composition for inhibiting rejection of transplanted cells.

It is another object of the present invention to provide a cell composition for transplantation including cells pretreated with the pharmaceutical composition for inhibiting rejection of transplanted cells.

It is yet another object of the present invention to provide a method of inhibiting rejection of transplanted cells.

Other objects and advantages of the present invention will become more apparent from the following detailed description of the invention, claims and drawings.

Technical Solution

One aspect of the present invention provides a pharmaceutical composition for inhibiting rejection of transplanted cells including a high mobility group box 1 A domain (HMGB1 A) as an active ingredient.

The present inventors have tried to develop a method of minimizing immunological rejection that may occur upon cell transplantation for cell transplantation treatment and increasing the success rate of cell transplantation. As a result, the inventors have demonstrated that the use of the high mobility group box 1 A domain (HMGB1A) dramatically alleviates immunological rejection upon cell transplantation and increases the engraftment rate of transplanted cells.

HMGB1A described in the present invention is a protein fragment derived from an HMGB1 protein. The inventors of the present invention initially revealed that HMGB1 A proteins are capable of binding to HMGB1 proteins. In addition, the present inventors developed a PTD-HMGB1 A protein prepared by introducing a protein transduction domain (PTD) into HGMB1A, thereby enabling HMGB1A proteins to be delivered into cells ex vivo. Based on the discovery and protein constructs, the inventors have revealed that intracellular delivery of PTD-HMGB1A proteins effectively inhibits the secretion of HMGB1 proteins outside cells. Therefore, the intracellular delivery technology using the PTD-HMGB1A can be expected to advance cell therapy by providing a method of inhibiting rejection of transplanted cells especially in pancreatic islet transplantation, which is used for treating diseases caused by defects of pancreatic islet cells such as diabetes. Furthermore, it is expected that the technology may be effective for all cell transplantation treatments including stem cell transplantation.

According to an embodiment of the present invention, the HMGB1A of the present invention may further be combined with the PTD.

The inventors of the present invention demonstrated that the use of the pharmaceutical composition including PTD-HMGB1A, in which HMGB1A and PTD are combined, upon cell transplantation dramatically improves the success rate of cell transplantation. PTD, a small peptide consisting of 10 to 16 basic amino acids, penetrates plasma membranes alone or in combination with other substances without the aid of specific receptors, resulting in accumulation in the cells. The binding of PTD to HMGB1A may be carried out using conventional methods known in the art, and tier example, the PTD-HMGB1A proteins may be obtained by preparing a vector expressing the PTD-HMGB1A.

According to an embodiment of the present invention, the PTD of the present invention may be any of those known in the art and may be selected from the group consisting of, for example, trans-acting activator of transcription (Tat), Hph1, penetratin, transportan, Virus Protein 22 (VP-22), amphipathic peptides, MPG, Pep-1 peptide, model amphipathic peptide (MAP), sweet arrow peptide (SAP), PPTG1, cationic peptides, oligoarginine, human calcitonin fragment 9-32 (hCT(9-32)), syrB and Vascular-Endothelial-Cadherin-derived cell-penetrating peptide (pVEC), but is not limited thereto.

According to an embodiment of the present invention, the PTD of the present invention may be Tat. Tat is a protein expressed by HIV-1, which consists of 86 to 101 amino acids depending on subtype (see Jeang, K. T. (1996) In: Human Retroviruses and AIDS: A Compilation and Analysis of Nucleic Acid and Amino Acid Sequences. Los Alamos National Laboratory (Ed.) pp. III-3-III-18), and causes the phenomenon of protein transduction. It has been known that the 49-57th amino acid sequence "RKKKRRQRRR" (SEQ ID NO:. 1) among the amino acid sequence of Tat is the minimal region that allows Tat to function as PTD.

In an embodiment of the present invention, the pharmaceutical composition of the present invention may be used in at least one of (a) pretreatment of cells prior to transplantation and (b) systemic administration to a subject into whom the cells have been transplanted. According to the present invention, the pretreatment of cells for transplantation refers to treatment of the transplantable cells with HMGB1A, specifically PTD-HMGB1A, more specifically Tat-HMGB1A, prior to transplantation into the subject, after preparing cells for transplantation into the subject. As a specific treatment method, separated cells, which are used for transplantation, are cultured in a laboratory, and then the existing culture medium is replaced with a culture medium containing purified PTD-HMGB1A (e.g., Tat-HMGB1A), followed by further culturing. According to the present invention, when systemically administering to a subject into whom the transplantable cells have been transplanted, the pharmaceutical composition of the present invention may be administered simultaneously with transplantation of cells or immediately after transplantation of cells. In addition, PTD-HMGB1A (e.g., Tat-HMGB1A) exhibits systemic effects even when administered to other sites, rather than directly to sites where cells are transplanted.

The pharmaceutical composition of the present invention is preferably used in pretreatment of cells prior to transplantation. The pharmaceutical composition is advantageous in terms of efficiency and safety in that transplantation rejection may be prevented by pretreating cells prior to transplantation compared to conventional drugs that can delivered by systemic administration after transplantation or by local administration at the site of transplantation, and thus is distinguishable from conventional drugs for inhibiting rejection of transplantation.

In an embodiment of the present invention, the cells of the present invention may be pancreatic islet cells, adult stem cells, embryonic stem cells or induced pluripotent stem cells (IPSCs). The cell transplantation of the present invention may be carried out for treatment of diseases without limitation as long as the diseases are defect diseases, and particularly for treatment of diseases in which regeneration of damaged cells is considered difficult or impossible. Pancreatic islet cells, adult stem cells, embryonic stem cells, and induced pluripotent stem cells (IPSCs) are currently being used clinically for cell transplantation treatment, or are expected to be used clinically, and are therefore suitable for cell transplantation treatment. Transplantation of the transplantable cells may be carried out by selecting appropriate transplantation sites known in the art and injecting the cells using known methods. For example, transplantation of pancreatic islet cells is performed by selecting appropriate transplantation sites (e.g., a kidney subcapsular region, the portal vein, and the like) known in the art and injecting the cells into the selected transplantation sites using known methods (e.g., a method of transplanting isolated islets into the liver through the portal vein percutaneously under ultrasound projection without abdominal incision). Islet cells suitable for transplantation should meet the following conditions: the cells should be ABO matched, gram-negative, and endotoxin-free and the cells should have a cell number of 5,000 kg (weight of a subject) or more, a purity of 30% or more, and a final volume of 10 ml or less (see Shapiro J et al., International Trial of the Edmonton Protocol for Islet Transplantation, *N Engl J Med* 355:1318-1330 (2006)).

The pharmaceutical composition for inhibiting rejection of transplanted cells of the present invention may be administered to a subject together with cells for transplantation and administered at cell transplantation sites after cell transplantation. The PTD-HMGB1A may be administered at any site other than cell transplantation sites.

The pharmaceutical composition of the present invention may include a pharmaceutically acceptable carrier. The pharmaceutically acceptable carrier included in the pharmaceutical composition of the present invention is commonly used in preparation and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto. The pharmaceutical composition of the present invention may further include lubricants, wetting agents, sweeteners, flavoring agents, emulsifying agents, suspending agents, preservatives, and the like in addition to the carriers. Suitable pharmaceutically acceptable carriers and preparations are described in detail in *Remington's Pharmaceutical Sciences* (19th ed., 1995).

When the pharmaceutical composition of the present invention is administered to a subject, the composition may be administered by intravenous, subcutaneous, intramuscular and intraperitoneal injection, transdermal administration, and the like.

A suitable dose of the pharmaceutical composition of the present invention may vary depending on factors such as formulation method, the manner of administration, patient's age, body weight, sex, pathological conditions, diet, administration time, routes of administration, excretion rate and responsiveness/sensitivity. The daily dose of the pharmaceutical composition of the present invention may be, for example, 0.001 to 1000 mg/kg.

The pharmaceutical composition of the present invention may be prepared in individual doses or prepared by injection into a large-capacity container by formulating the pharmaceutical composition with a pharmaceutically acceptable carrier and/or excipient, according to a method which can be easily carried out by a person skilled in the art to which the present invention belongs. Dosage forms may include solutions, suspensions, syrups or emulsions in oils or aqueous media, or extracts, powders, granules, tablets or capsules, and may additionally include dispersing or stabilizing agents.

According to an embodiment of the present invention, the pharmaceutical composition of the present invention may be used for treatment of diseases selected from the group consisting of type 1 diabetes, type 2 diabetes, diabetic chronic kidney diseases, leukemia, aplastic anemia, Huntington's disease, stroke, spinal cord injuries and multiple sclerosis.

The composition of the present invention, as described in another embodiment, may be used for treatment of diseases without limitation as long as the diseases are cell defect diseases, and particularly for treatment of diseases in which regeneration of damaged cells is considered difficult or impossible. In particular, the composition of the present invention may be used for treatment of type 1 diabetes, type 2 diabetes, diabetic chronic kidney diseases, leukemia, aplastic anemia, Huntington's disease, stroke, spinal cord injuries or multiple sclerosis.

According to an embodiment of the present invention, the disease considered in the present invention is type 1 diabetes. Type 1 diabetes is caused by loss of insulin-secreting capacity due to the destruction of insulin-secreting pancreatic islet beta cells, and pancreatic islet transplantation may be a good method for treating type 1 diabetes.

Another aspect of the present invention provides a cell composition for transplantation including cells pretreated with the pharmaceutical composition for inhibiting rejection of transplanted cells.

The cells for transplantation of the present invention may be derived from humans or other donor animals, for example, pigs. Currently, in the case of pancreatic islet cells, not only pancreatic islet cells isolated from human pancreases but also pancreatic islet cells isolated from pigs are used for treatment using pancreatic islet transplantation. The pancreatic islet cell composition tier transplantation of the present invention may additionally include pancreatic islet cells isolated from pigs.

In an embodiment of the present invention, the cells of the present invention may be pancreatic islet cells, adult stem cells, embryonic stem cells or induced pluripotent stem cells (IPSCs).

Since the cell composition for transplantation of the present invention is prepared by pretreating the cells for transplantation with the composition described above, duplicate descriptions are omitted in order to avoid excessive complexity in the description herein.

Still another aspect of the present invention provides a method of inhibiting rejection of transplanted cells including (a) a step of pretreating cells prior to transplantation with a composition including a high mobility group box 1 A domain (HMGB1A) as an active ingredient or (b) a step of administering the composition including HMGB1A as an active ingredient systemically to a subject into whom the cells have been transplanted.

In an embodiment of the present invention, the HMGB1A of the present invention may further be combined with the protein transduction domain (PTD).

In an embodiment of the present invention, the cells of the present invention may be pancreatic islet cells, adult stem cells, embryonic stem cells or induced pluripotent stem cells (IPSCs).

Since the method of inhibiting rejection of transplanted cells of the present invention corresponds to a method of using the composition for inhibiting rejection of transplanted cells, which is another embodiment of the present invention described above, redundant content is omitted in order to avoid excessive complexity in the description herein.

Advantageous Effects

The features and advantages of the present invention are summarized as follows:

(a) The present invention provides a pharmaceutical composition for inhibiting rejection of transplanted cells including a high mobility group box 1 A domain (HMGB1A) as an active ingredient.

(b) The present invention provides a cell composition for transplantation including cells pretreated with the pharmaceutical composition for inhibiting rejection of transplanted cells, in which the pharmaceutical composition includes the high mobility group box 1 A domain (HMGB1A) as an active ingredient.

(c) The present invention provides a method of inhibiting rejection of transplanted cells.

(d) According the present invention, immunological rejection may significantly be alleviated upon cell transplantation.

(e) According to the present invention, the engraftment rate of transplanted cells and the success rate of cell transplantation may be increased.

MODES OF THE INVENTION

Hereinafter, the present invention will be described in more detail with reference to the following examples. Those skilled in the art will understand that these examples are only for describing the present invention in more detail and that the scope of the present invention is not limited by these examples in accordance with the gist of the present invention.

EXAMPLES

Example 1: Preparation of TAT-HMGB1A Fusion Protein 1-1. Preparation of HMGB1A and TAT-HMGB1A Plasmids Total RNA was extracted from Human embryonic kidney (HEK) 293 cells and subjected to RT-PCR to obtain cDNA. To amplify the cDNA region corresponding to amino acids 1 to 164 of a human recombinant HMGB1 (rHMGB1) protein, cDNA was subjected to PCR using the following primers, which are specific to the HMGB1 gene.

```
Forward (EcoRI site, underlined):
                                    (SEQ ID NO:. 2)
5'-CCGGAATTCATGGGCAAAGGAGATCCTAAG-3'

Reverse (HindIII site, underlined):
                                    (SEQ ID NO:. 3)
5'-CCCAAGCTTGATGTAGGTTTTCATTTCTCTTTC-3'
```

Figure 1:
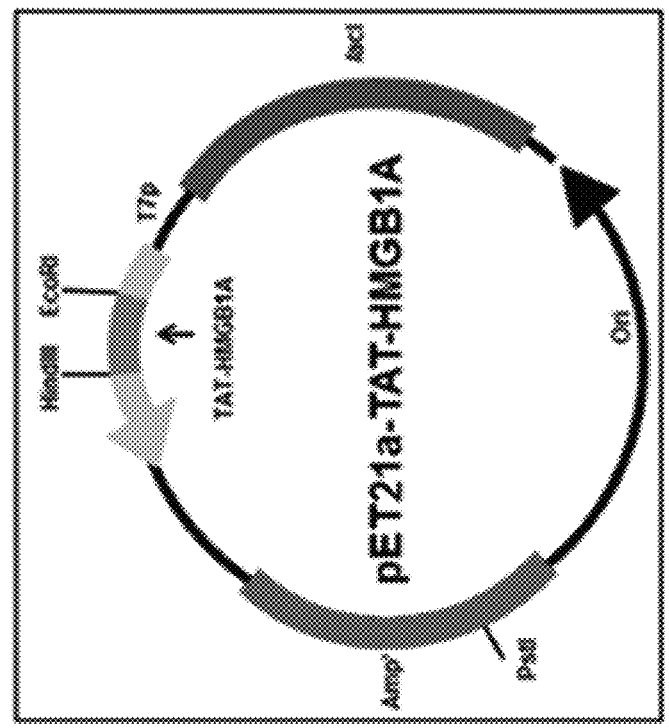
FIG. 1 illustrates plasmids prepared for expression of HMGB1A and TAT-HMGB1 A, respectively.
Figure 1:
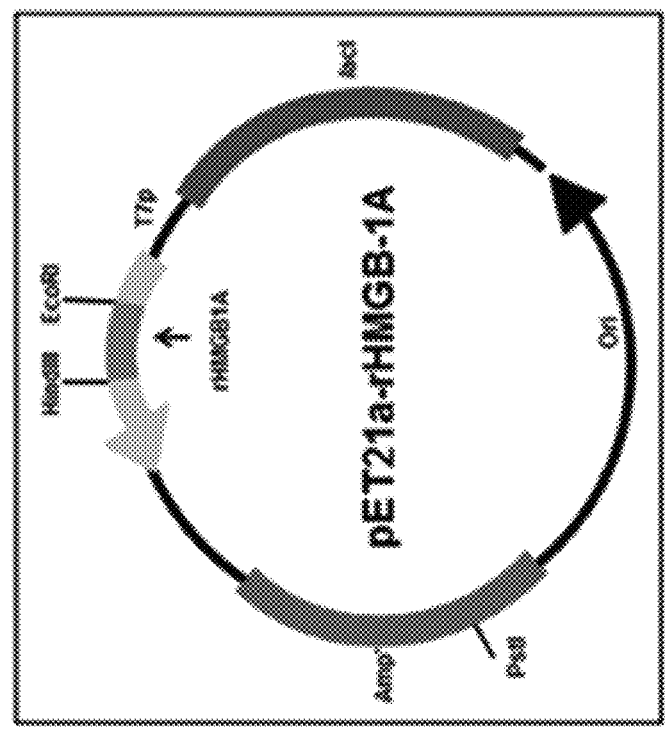

The amplified cDNA fragments were digested with EcoRI and HindIII restriction enzymes, and the digested products were subjected to agarose gel electrophoresis. Purified rHMGB1A cDNA was inserted into a pET21a vector, and then an oligonucleotide encoding six histidine residues was introduced at the 3' end of the inserted rHMGB1A cDNA to prepare an expression vector harboring rHMGB1A tagged with 6 histidine residues at the C-terminus thereof (i.e., rHMGB1A-his6). After expression of the vector, an expressed rHMGB1A-his6 protein was subjected to affinity chromatography. Next, the TAT peptide sequence was prepared. Upstream DNA (BamHI site, underlined): 5'-GATCCAAGCTTCGCAAAAAGCGGAGACAGAGAC-GCAGGG-3', (SEQ ID NO:. 4) and downstream DNA (EcoRI site, underlined): 5'-AATTCCCTGCGTCTCTGTCTCCG-CTTTTTGCGAAGCTTG-3', (SEQ IS NO:. 5) were used. After linking TAT cDNA to a cDNA fragment encoding the A box domain of HMGB1, the linked cDNA was inserted into a pET21a plasmid (rTAT-HMGB1A-his6). An expressed rTAT-HMGB1A-his6 protein was purified using affinity chromatography. The maps of these vectors were identified through a DNA sequence analysis(see FIG. 1).

1-2. Expression of Recombinant Proteins

The *E. coli* BL21(λDE3) strain was used for the expression of recombinant proteins. Bacteria were cultured in Luria-Bertani (LB) broth containing 50 µg/ml ampicillin (i.e., LB Amp). A single colony, which had pET21a-HMGB1A or pET21a-TAT-HMGB1A, was cultured in LB Amp at 37° C. until an $OD_{600\,nm}$ value was 0.6. After adding 500 µM IPTC, the single colony culture was further cultured at 37° C. for 6 hours. The single colony culture was subjected to centrifugation to obtain a pellet, and the pellet was dissolved in a lysis buffer containing 1 mM PMSF and subsequently was sonicated three times for 30 seconds each. Cell debris was removed by performing centrifugation at 10,000 g and 4° C., and then a supernatant was purified.

1-3. Purification of Recombinant Proteins rTAT-HMGB1A-his6 peptides were purified using nickel chelate affinity chromatography. Unbound proteins were removed using a buffer. After adding imidazole, the concentrations of fusion proteins were determined by BCA analysis and the sizes of the fusion proteins were analyzed using SDS-PAGE. The fusion proteins were dialyzed by 6,000 to 8,000 Da membranes in PBS containing 20% glycerol and 0.2 mM PMSF. After dialysis, protease inhibitor cocktails were added to solutions containing the fusion proteins and stored at −80° C. until use.

Example 2: Isolation of Pancreatic Islets Cells 7-week-old male SD-rats were anesthetized with an anesthetic and then the abdomen of the SD-rats was incised. After exposing the pancreas, the pancreas was inflated by adding a collagenase P solution through the common bile duct and then the pancreas was excised. After performing an enzyme reaction for 17 minutes, a cold M199 medium was added to stop the enzyme reaction, followed by washing twice. Density gradient centrifugation using a double-layer composed of Ficoll-Histopaque and a M199 medium was carried out for 24 minutes. The pancreatic islets between the separated layers were collected and subjected to handpicking using a stereo microscope after washing two times. The isolated pancreatic islets were cultured in a RPMI-1640 culture medium containing 10% FBS and 1% antibiotics for one day. The next day, the culture medium was changed once.

Example 3: Establishment of TAT-HMGB1A Treatment Conditions in Pancreatic Islets When pancreatic islets were treated with TAT-HMGB1A, cell viability was measured depending on the concentration of TAT-HMGB1A. Pancreatic islets were added to RPMI-1640 solutions respectively containing 0, 5, 10, 15, 20 and 25 µM TAT-HMGB1A and were incubated in a $CO_2$ incubator set to 37° C. for 24 hours. The TAT-HMGB1A-treated pancreatic islets were washed two times, and cell morphology was observed using an optical microscope and cell viability was measured using a CCK-8 analysis kit. A medium containing TAT-HMGB1A at a concentration of 10 µM was added to pancreatic islets, incubated for 0, 4, 8, 12 or 24 hours in a $CO_2$ incubator set to 37° C. and washed twice with RPMI-1640, and then cell viability was measured using a CCK-8 analysis kit.

Figure 2A:
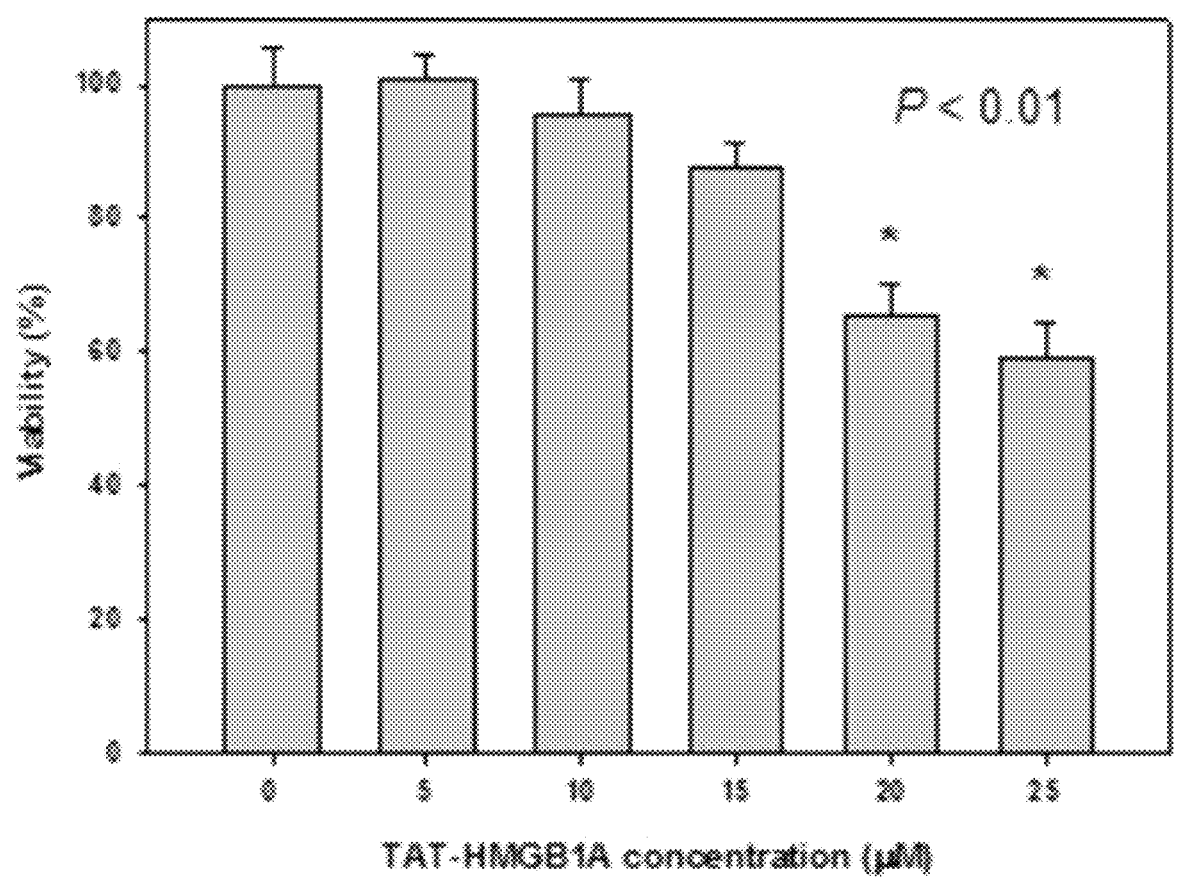
FIGS. 2A to 2C are experimental results showing the effect of TAT-HMGB1A on cell viability when pancreatic islet cells were treated with TAT-HMGB1A.
Figure 2B:
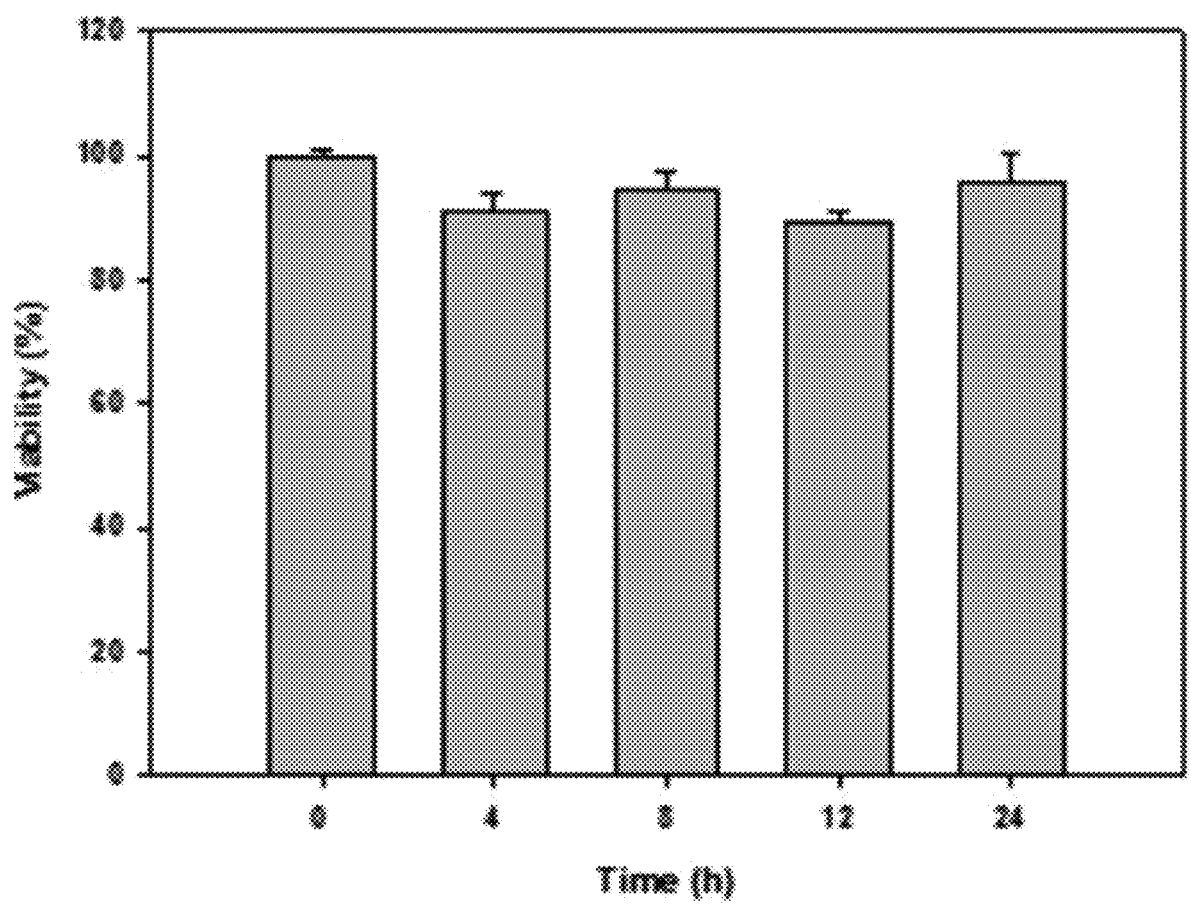
Figure 2C:
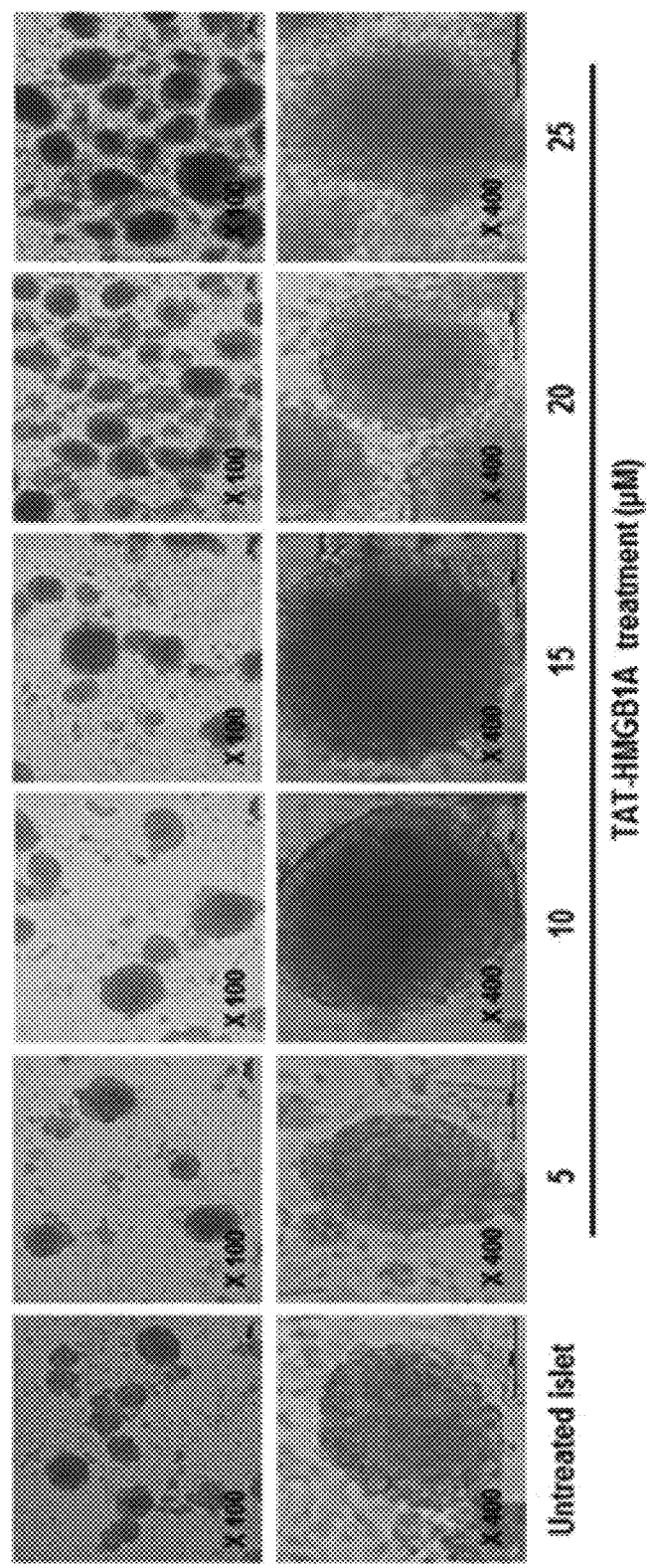

This example explains experiments to determine whether TAT-HMGB1A affects cell viability when pancreatic islet cells were treated with TAT-HMGB1A. As shown in the graph of FIG. 2A, when pancreatic islet cells were treated with different concentrations of TAT-HMGB1A, the viability of pancreatic islet cells decreased as the concentration increased. In particular, when pancreatic islet cells were treated with TAT-HMGB1A at a concentration of 20 µM or more, cell viability was significantly reduced. These results were confirmed by the images of FIG. 2C taken with an optical microscope. It was confirmed that the outer collagen layers of cells were broken in the pancreatic islet cells treated with a high concentration of TAT-HMGB1A. Based on the graph of FIG. 2B showing cell viability depending on the treatment period of 10 µM TAT-HMGB1A, it was determined that the treatment period of the protein does not significantly affect cell viability. It is difficult to introduce proteins into pancreatic islet cells because individual pancreatic islet cells, unlike other normal cells, aggregate into clusters. Therefore, based on the cell viability experiments, the concentration and treatment period of TAT-HMGB1A, which maximize the delivery of TAT-HMGB1A, were determined to be 10 µM and 24 hours, respectively.

Example 4: Confirmation of Introduction of TAT-HMGB1A into Pancreatic Islet Cells (Preparation of Fluorescent Alexa 488-Labeled TAT-HMGB1A and Observation of Amount of Labeled TAT-HMGB1A Introduced in Pancreatic Islets Cells)

A 1 M sodium bicarbonate solution (pH 8.3) was prepared. 100 µl of TAT-HMGB1 A and 10 µl of the 1M sodium bicarbonate solution were mixed. 4 µl of Alexa 488 was added, and a reaction was performed for 15 minutes and then Alexa 488-labeled TAT-HMGB1A was purified using a spin filter. Pancreatic islets were treated with a RPIM-1640 medium containing the Alexa 488-labeled TAT-HMGB1A at a concentration of 10 µM and incubated for 24 hours. After washing twice with a fresh RPMI-1640 medium, whether the Alexa 488-labeled TA T-HMGB1A was introduced into pancreatic islets cells was determined using a confocal microscope. Pancreatic islet cells treated with the Alexa 488-labeled TAT-HMGB1A were separated into single cells using a TrypLE Express solution and then subjected to FACS analysis.

Figure 3A:
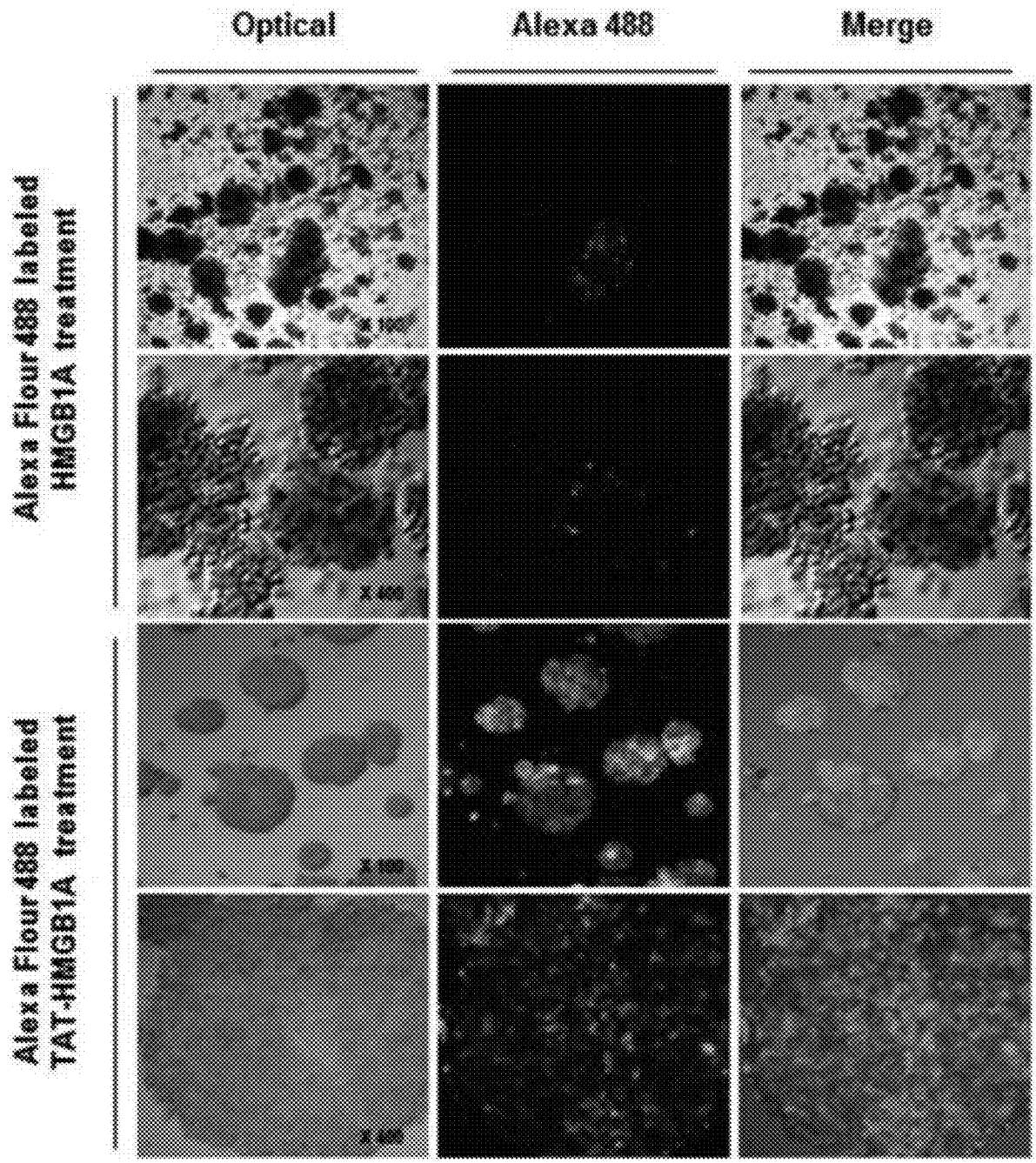
FIGS. 3A and 3B are results showing whether HMGB1A and TAT-HMGB1A were introduced into pancreatic islet cells. HMGB1 A and TAT-HMGB1A proteins were labeled with Alexa Fluor 488 dye, which fluoresces at 488 nm. Pancreatic islet cells mere treated with each of these labeled proteins, and images were taken using a confocal microscope.
Figure 3B:
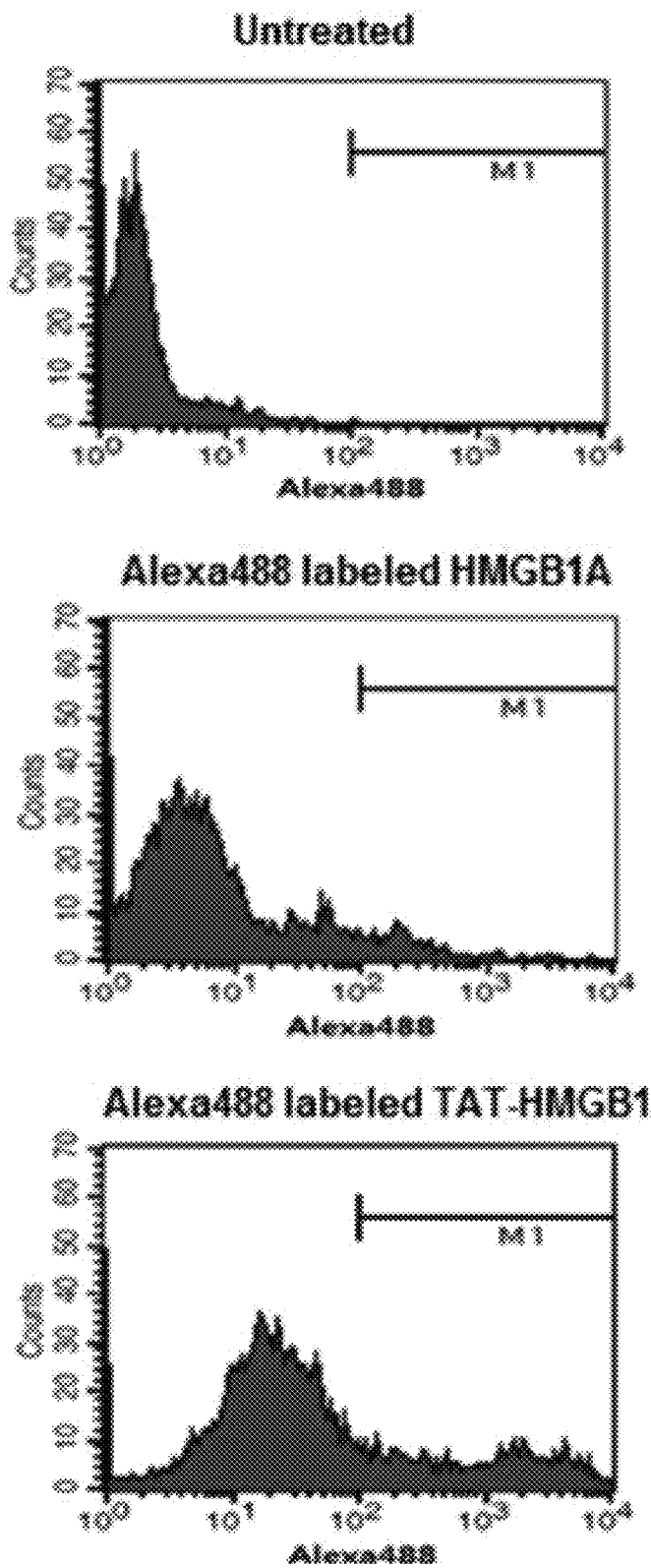

HMGB1A and TAT-HMGB1A proteins were labeled with Alexa Fluor 488 dye, which fluoresces at 488 nm. Pancreatic islet cells were treated with each of these labeled proteins, and then, as shown in FIG. 3A, images were taken using a confocal microscope to observe these proteins introduced into the cells. As shown in FIG. 3A, more TAT-HMGB1A was found to be introduced into pancreatic islet cells than control HMGB1A proteins. A quantitative analysis using FACS showed that the inflow rate of TAT-HMGB1A was 22.31%, which is much better than when simply treating with HMGB1A (6.1%).

Example 5: Evaluation of Insulin Releasing Capacity of Pancreatic Islets after TAT-HMGB1 A Treatment In Vitro Pancreatic islets were treated with 10 µM TAT-HMGB1A for 24 hours and washed with a RPMI-1640 medium. Control pancreatic islets and TAT-HMGB1A-treated pancreatic islets were washed twice with a 2.8 mM glucose Krebs buffer. 50 islet equivalents (IEQ) of each group were put in an insert, and a low glucose (2.8 mM) Krebs buffer was added to each insert, followed by culturing at 37° C. for 1 hour. After a reaction, the solutions were added to E-tubes, and the inserts were transferred to a high glucose (20.2 mM) Krebs buffer, followed by incubation at 37° C. for 1 hour. The solutions that had been reacted in the high glucose buffer were put into E-tubes, and the insulin amounts of the solutions were quantitatively analyzed using an insulin ELISA kit. After recovering the pancreatic islets of each group from the inserts, the pancreatic islets were lysed using a RIPA buffer. After removing cell debris, DNA was recovered and quantitated using a DNA analysis kit (Quant-iT™ dsDNA assay kit, Invitrogen).

Figure 4A:
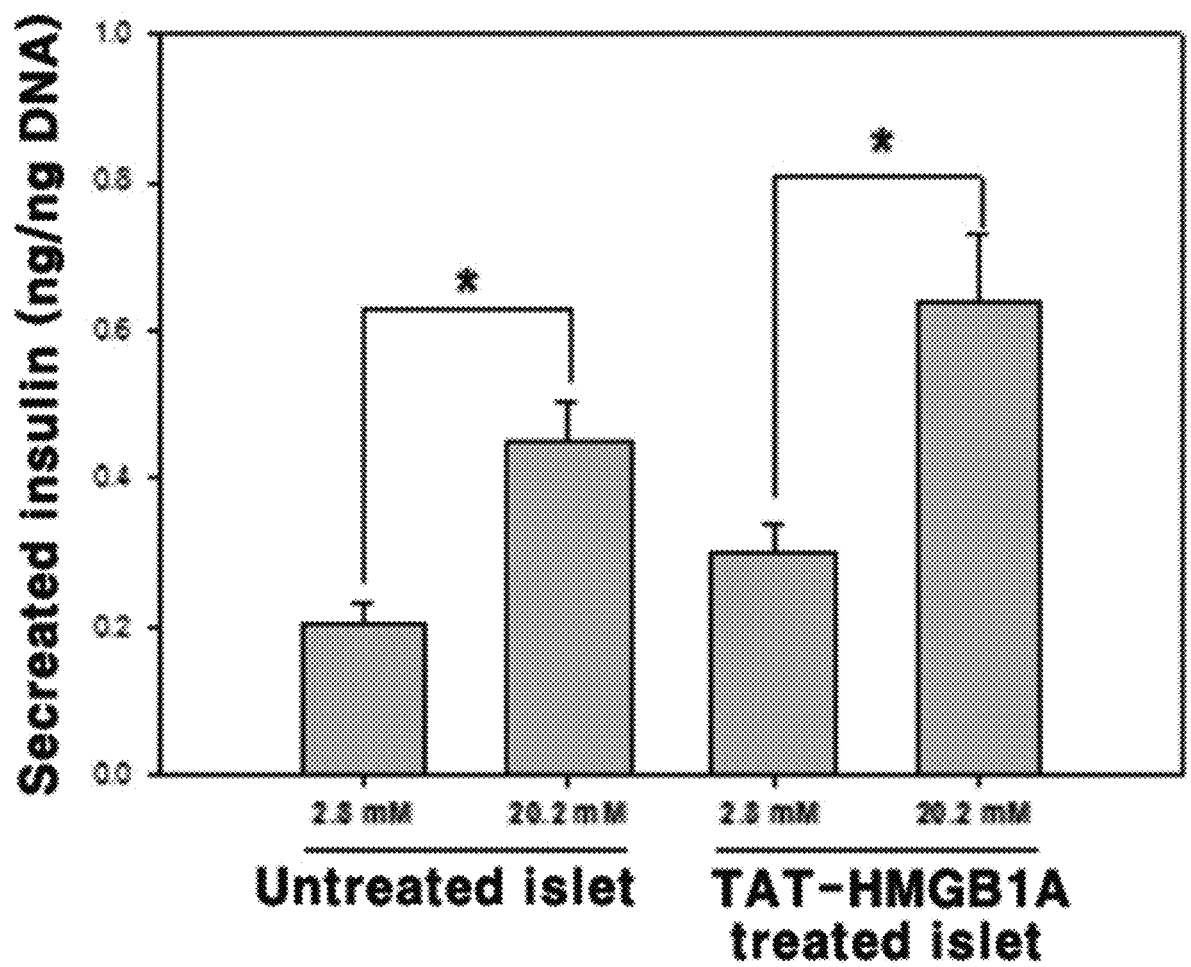
FIGS. 4A and 4B show the results of measuring glucose stimulated insulin secretion (GSIS) to determine whether treatment with TAT-HMGB1A affects the insulin secretion capacity of pancreatic islet cells.
Figure 4B:
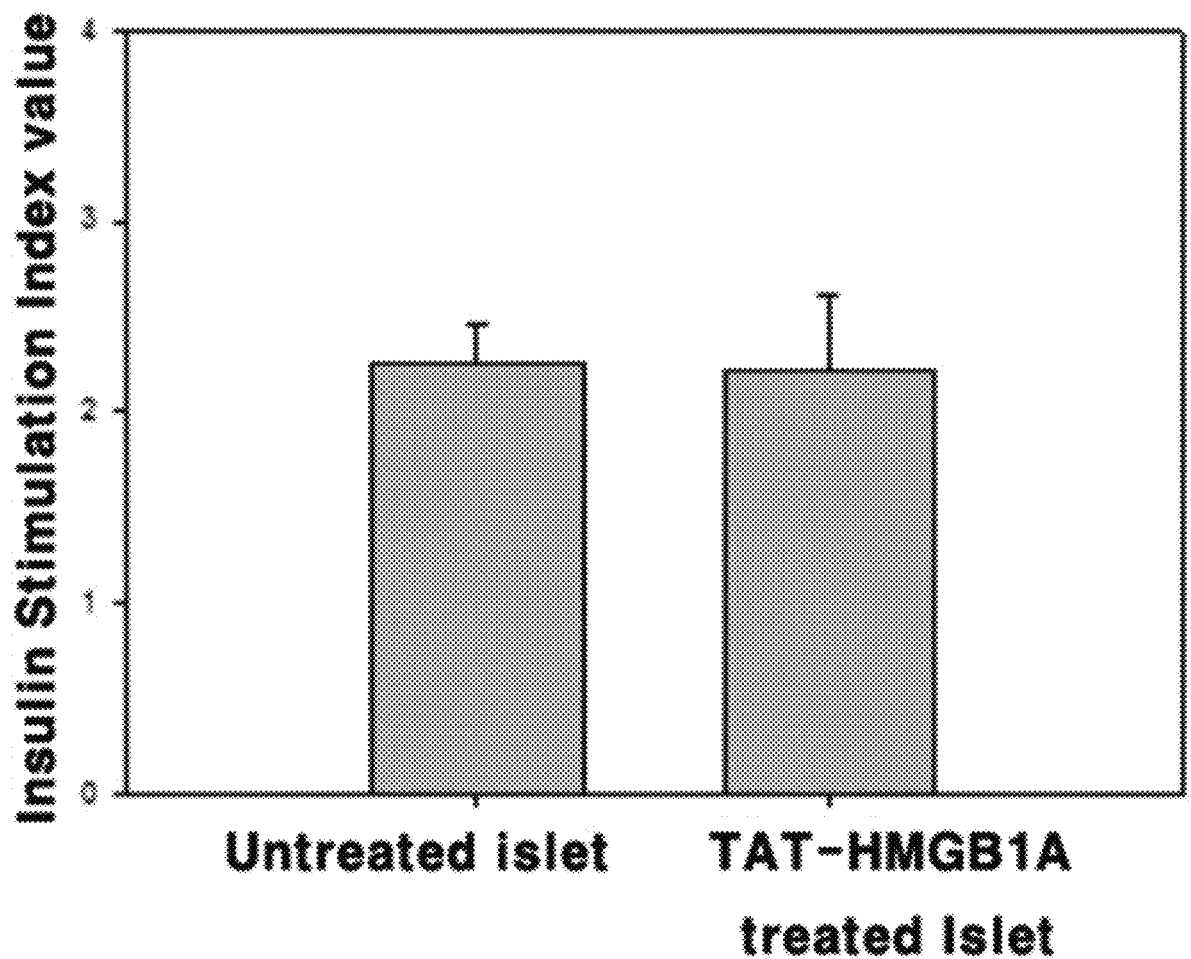

FIG. 4 shows the results of measuring glucose stimulated insulin secretion (GSIS) to determine whether treatment with TAT-HMGB1A affects the insulin secretion capacity of pancreatic islet cells. As shown in FIG. 4A, similar to control pancreatic islet cells, TAT-HMGB1A-treated pancreatic islet cells exhibited a similar pattern of insulin secretion in low glucose and high glucose solutions. In addition, to determine the increased amount of insulin secreted then cells cultured in a low glucose solution were transferred to a high glucose solution, insulin stimulation index values were calculated. As shown in FIG. 4B, similar to control pancreatic islet cells, TAT-HMGB1A-treated pancreatic islet cells exhibited more than a two-fold increase in insulin secretion. These results indicate that TAT-HMGB1A treatment does not affect the insulin releasing capacity of pancreatic islet cells.

Example 6: Measurement of HMGB1 Secretion in Damaged Pancreatic Islet Cells

Control pancreatic islet cells and TAT-HMGB1A-treated pancreatic islet cells were treated with 1.5 mM streptozotocin (STZ) for 8 hours. After a reaction, a culture medium was collected and HMGB1 ELISA was performed for the collected medium. Harvested cells were subjected to western blotting using HMGB1 antibodies.

Figure 5A:
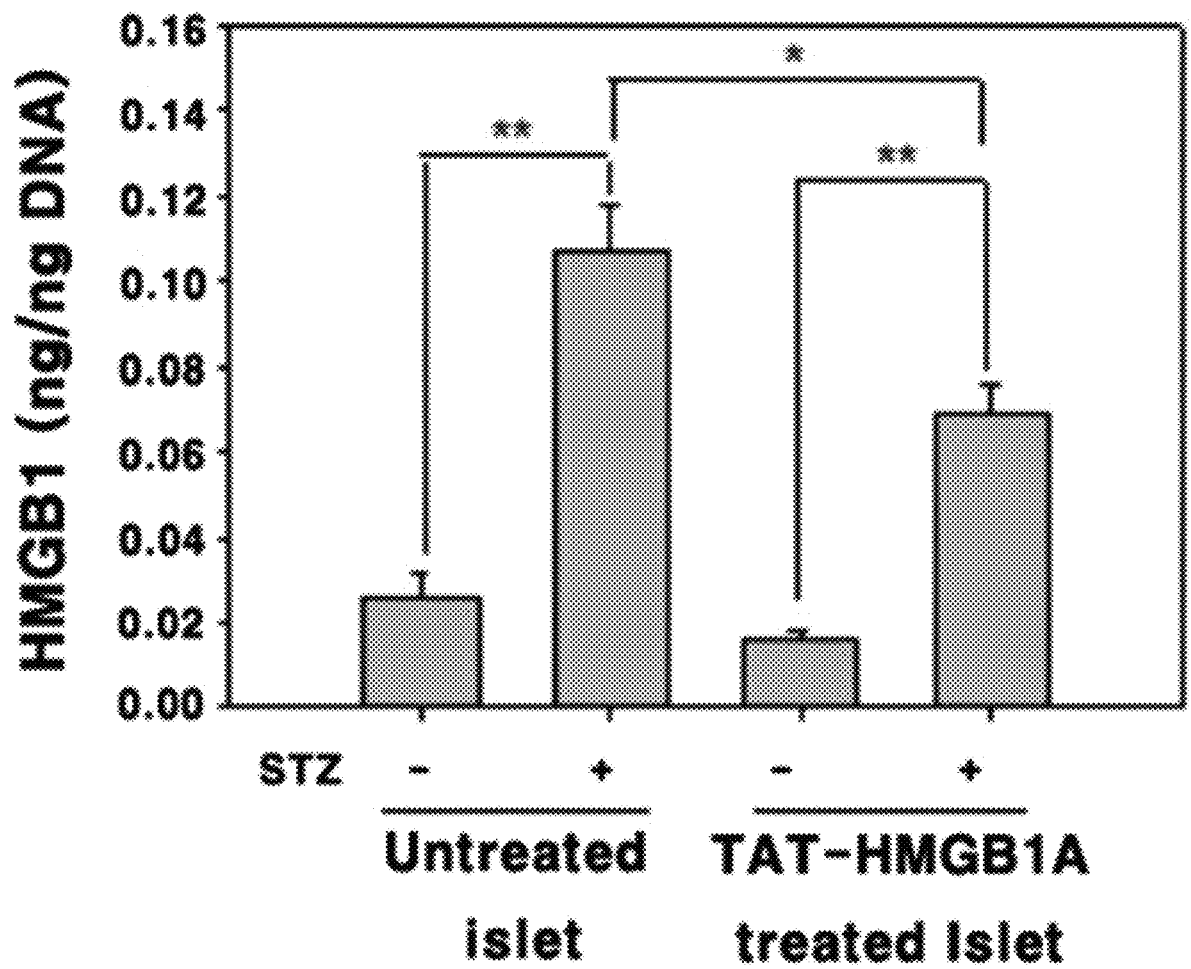
FIGS. 5A to 5D show the results of measuring the amounts of HMGB1 in the extracellular matrices of pancreatic islet cells. Control pancreatic islet cells and TAT-HMGB1A-treated pancreatic islet cells were exposed to streptozotocin (STZ) in vitro, and the amounts of HMG-B1 in the extracellular matrices of these STZ-damaged cells were measured using an HMGB1 ELISA kit.
Figure 5B:
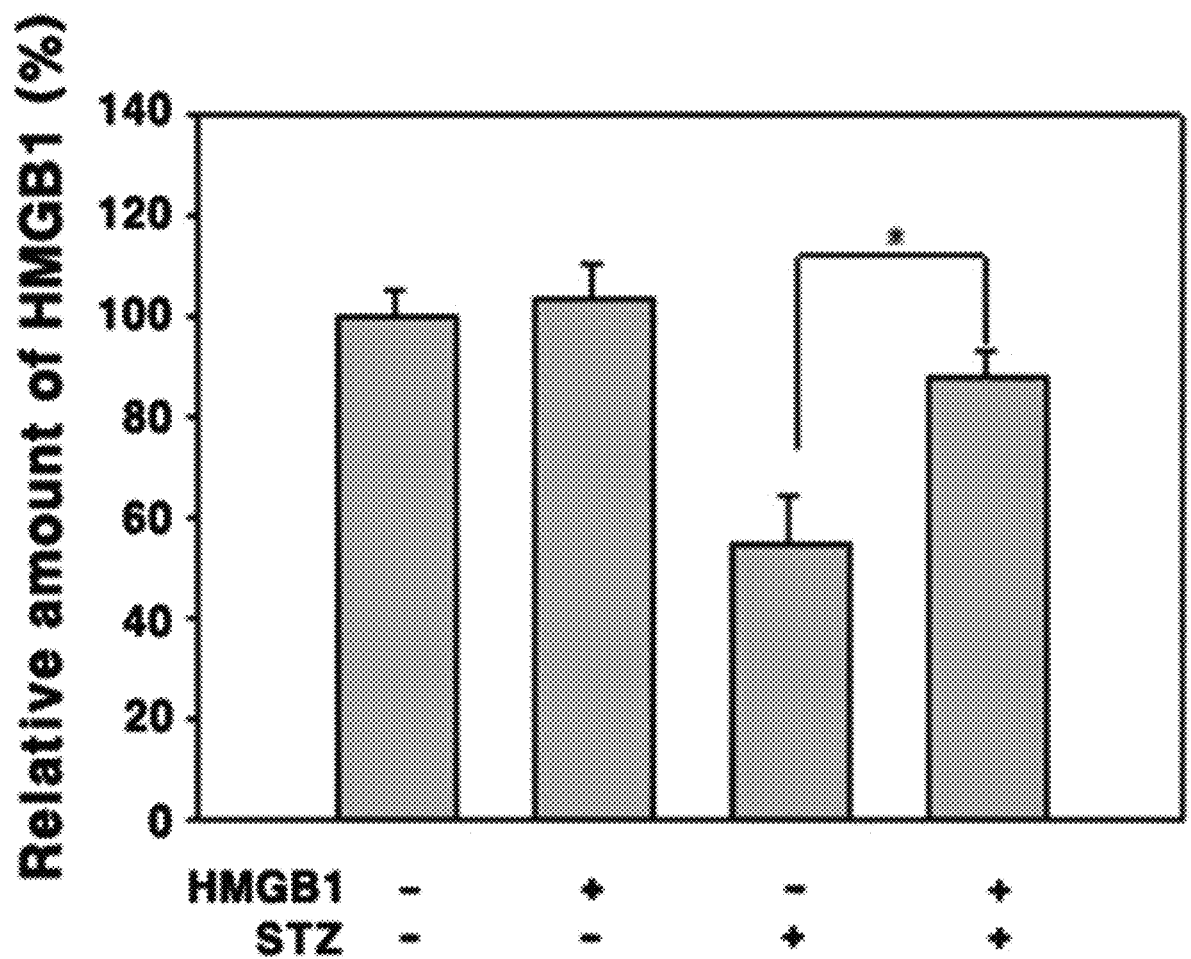
Figure 5C:
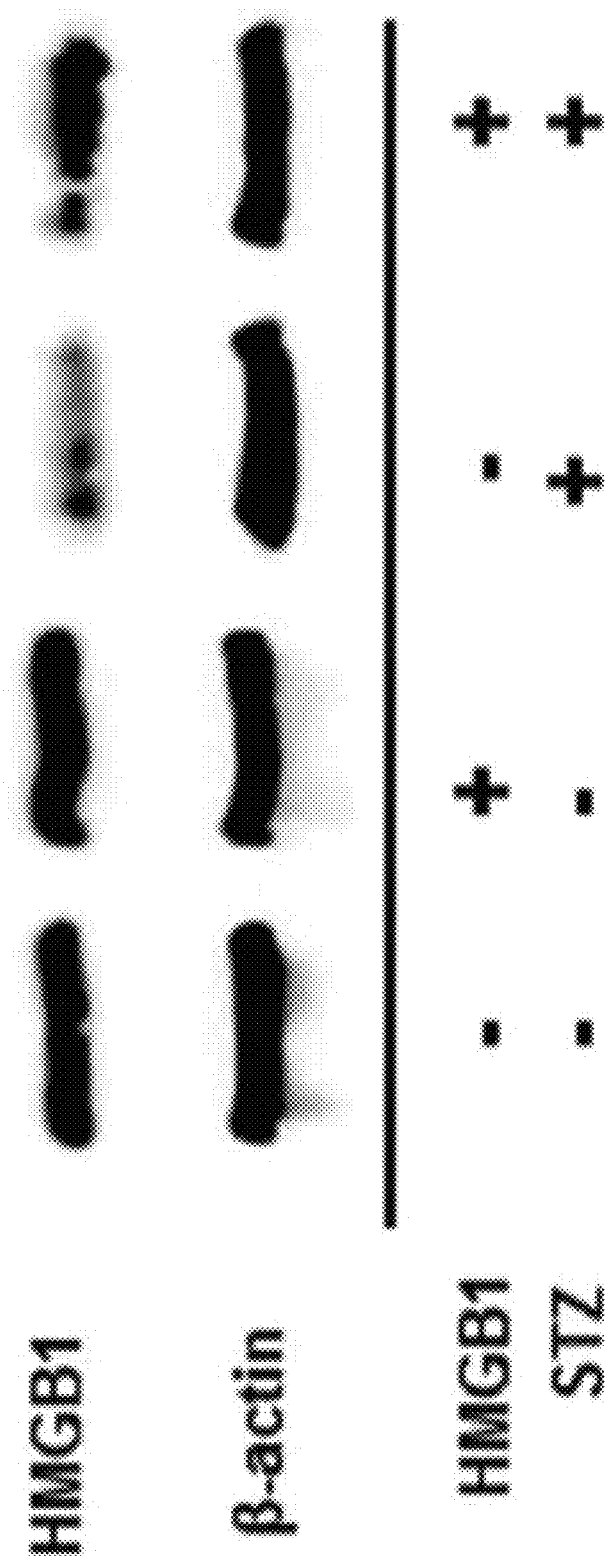
Figure 5D:
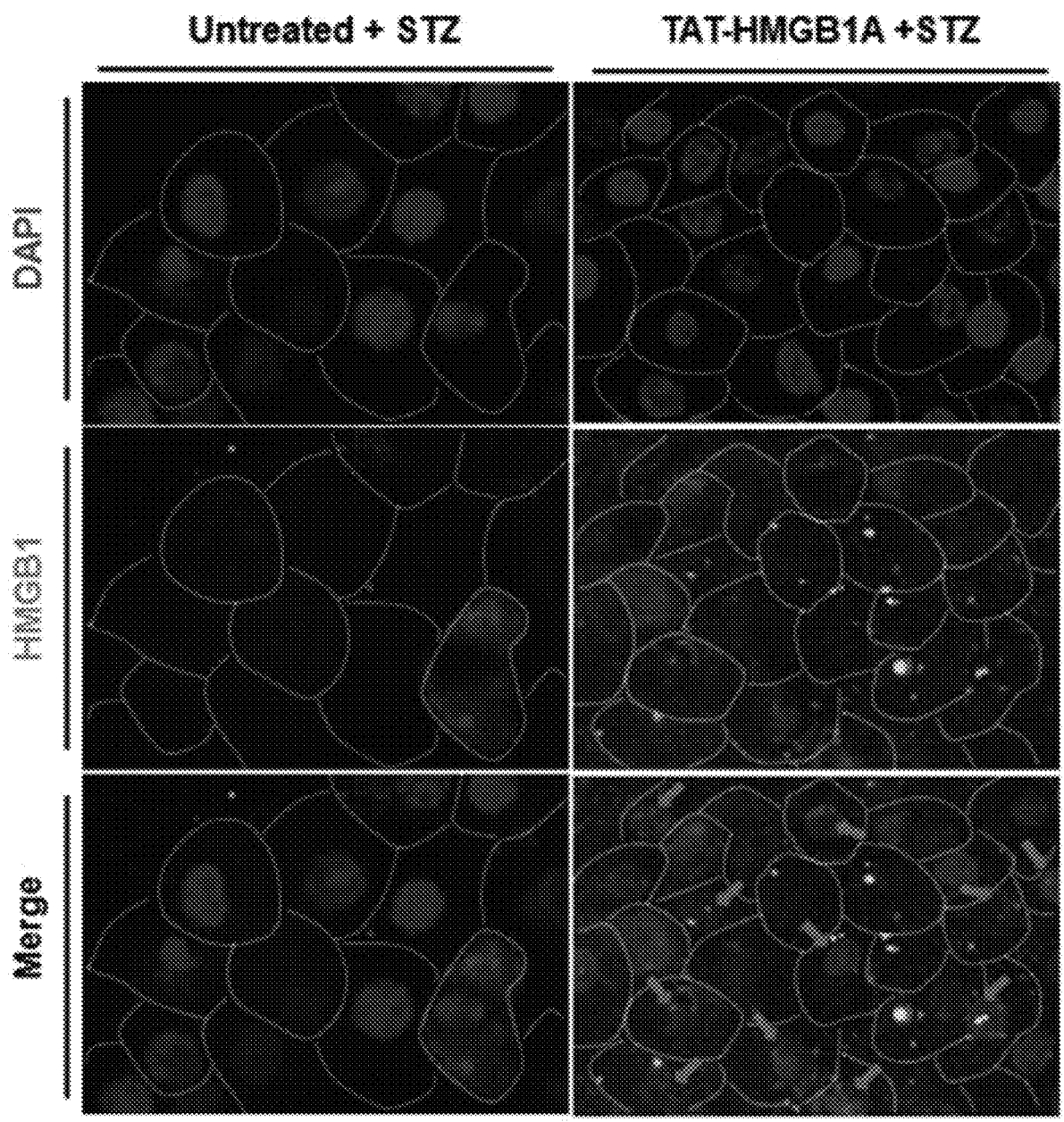

HMGB1 proteins abundant in the nuclei of pancreatic islet cells are released into the extracellular matrices of the cells when the cells are damaged. STZ is known as a reagent causing type 1 diabetes by inducing apoptosis in animal models. When control pancreatic islet cells and TAT-HMGB1A-treated pancreatic islet cells were exposed to STZ in vitro, most of cells were damaged. The amounts of HMGB1 in the extracellular matrices of these STZ-damaged cells were measured using an HMGB1 ELISA kit. As shown in FIG. 5A, compared with control pancreatic islet cells, the amount of HMGB1 present in the xtracellular matrices of TAT-HMGB1A-treated pancreatic islet cells was significantly reduced. In addition, as shown in FIGS. 5B and 5C, when western blotting was performed on cells harvested from each group treated with STZ, the amount of intracellular HMGB1 was much larger in the TAT-HMGB1A group than in the control group. In addition, when immunostaining was performed on cells obtained from each group treated with STZ using HMGB1 antibodies, the degree of HMGB1 staining was weak in the control pancreatic islet cells because most of intracellular HMGB1 proteins were released from the cells by STZ treatment. On the other hand, signals for HMGB1 staining were observed in both the nuclei and cytoplasms in the TAT-HMGB1A-treated group. These results suggest that introduction of TAT-HMGB1A into cells effectively reduces the amount of HMGB1 released from pancreatic islet cells upon cell damage.

Example 7: Identification of Binding Affinity Bet Teen HMGB1 and TAT-HMGB1A 7-1. Surface plasmon resonance (SPR)

A CMDH chip was used as a gold chip. Reichert's SR7500DC system equipment was used for measurement, and Scrubber2 software was used for analysis. PBS-T (0.05% Tween 20) was used as a buffer, and 10 μg of HMGB1, as a ligand, was applied at a flow rate of 20 μl/min for 10 minutes on the chip to coat. Thereafter, antibodies specific to each of TAT-HMGB1A, HMGB1A, TAT-MT and HMGB1 proteins were used as analytes, and binding between HMGB1 and each of TAT-HMGB1A, HMGB1A, TAT-MT and HMGB1 proteins was analyzed at various concentrations. The TAT-MT, a fusion protein of a metallothionein protein and the TAT peptide, was used as a control group to compare the binding affinity of TAT-HMGB1A to HMGB1.

TABLE 1

|  | Ka ($M^{-1}S^{-1}$) | Kd ($S^{-1}$) | KD |
|---|---|---|---|
| HMGB1A + TAT-HMGB1A | $(9.20 \pm 4) \times 10^3$ | $(6.91 \pm 3) \times 10^{-4}$ | $75.1 \pm 3$ nM |
| HMGB1 + HMGB1A | $(1.4 \pm 2) \times 10^3$ | $(3.942 \pm 3) \times 10^{-3}$ | $2.8 \pm 3$ μM |
| HMGB1 + TAT-MT | — | — | — |
| HMGB1 + HMGB1Ab | $(7.298 \pm 6) \times 10^4$ | $(6.38 \pm 9) \times 10^{-5}$ | $876.9 \pm 7$ pM |

Figure 6:
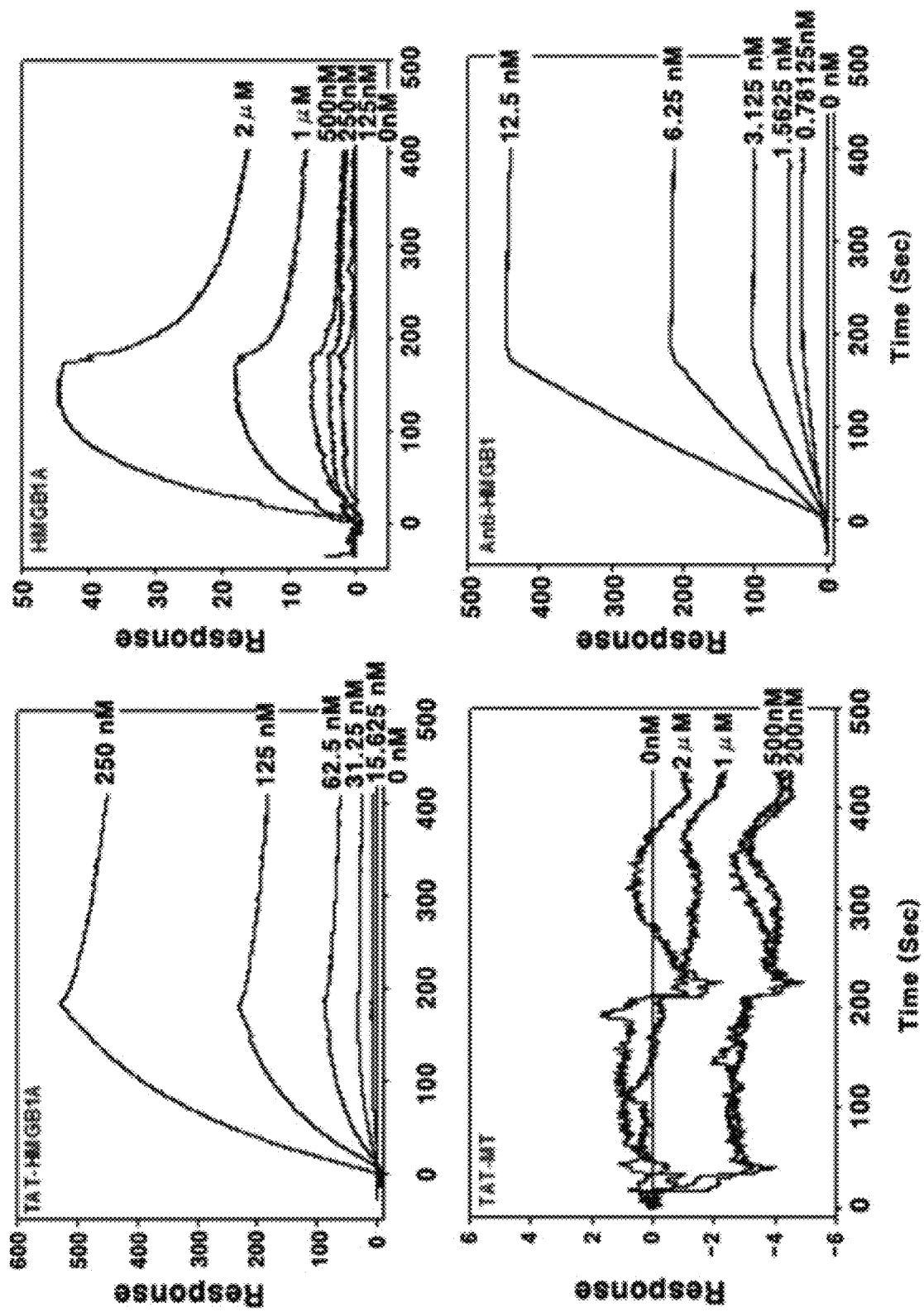
FIG. 6 shows the results of analysis of binding between HMGB1 and TAT-HMGB1A, HMGB1A, TAT-MT or HMGB1. Surface plasmon resonance (SPR) analysis was performed for antibodies specific to each of TAT-HMGB1A, HMGB1A, TAT-MT and HMGB1 at various concentrations.

As the result of SPR analysis, it was found that HMGB1 proteins bound to TAT-HMGB1 and HMGB1A proteins (see Table 1 and FIG. 6). Although the binding affinity of TAT-HMGB1 or HMGB1A to HMGB1 was much smaller than that of HMGB1 antibodies, it is significant to reveal that HMGB1 binds to TAT-HMGB1 and HMGB1A proteins. Compared with the control HMGB1A, the binding affinity of TAT-HMGB1A was stronger and more stable. However, the TAT-MT proteins did not bind to HMGB1 proteins. These results indicate that binding between TAT-HMGB1 and HMGB1 is not due to the positive charge of TAT.

7-2. Confirmation of Binding using Western Blotting

HMGB1 proteins were mixed with each of TAT-MT, HMGB1A. and TAT-HMGB1A proteins in a mass ratio of 1:1 and incubated at room temperature for 1 hour. 2 μg of each of HMGB1, TAT-MT, HMGB1A, TAT-HMGB1A, HMGB1+TAT-MT, HMGB1+HMGB1 A and HMGB1+TAT-HMGB1A proteins was loaded into each well of a 10% acrylamide gel and subjected to SDS-PAGE. After performing SDS-PAGE, proteins on the acrylamide gel were transferred to a PVDF membrane. The membrane was incubated in a buffer containing 5% skim milk for 1 hour at room temperature for a blocking reaction, and then incubated with rabbit HMGB1 antibodies diluted at a 1:1000 ratio for 1 hour at room temperature. After washing three times for 10 minutes each with TBS-T, the membrane was incubated with anti-rabbit secondary antibodies diluted at a 1:5000 ratio for 1 hour at room temperature. After washing three times for 10 minutes each with TBS-T, a chemilutninescent reagent was added to the membrane, and subsequently a chemiluminescent image was taken (see FIG. 7).

Figure 7:
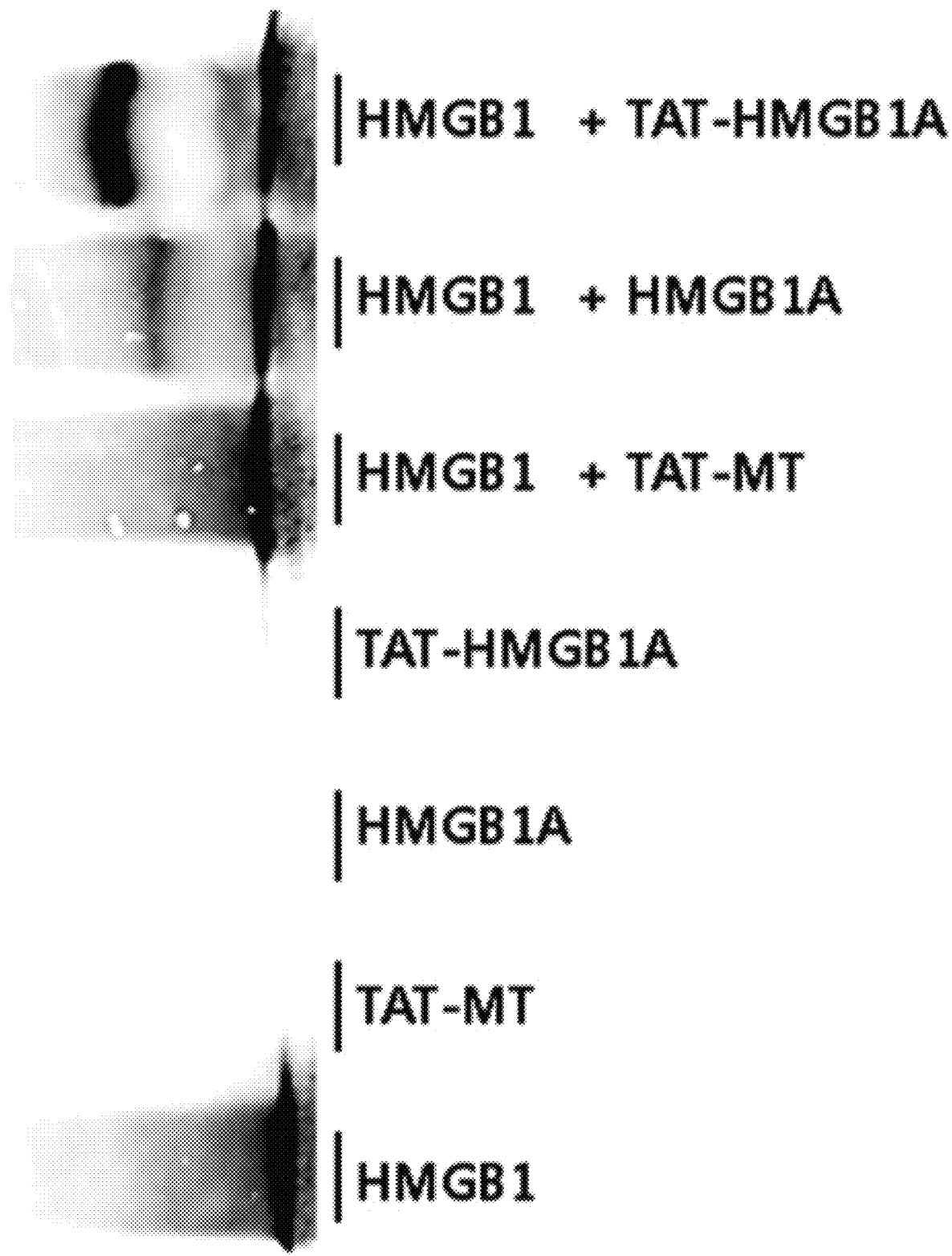
FIG. 7 shows a western blotting result for determining binding between HMGB1 and analysis targets.

According to the western blotting result as shown in FIG. 7, two bands were observed only in the lines corresponding to the wells in which HMGB1+HMGB1A and HMGB1+TAT-HMGB1A proteins had been loaded, respectively. This result indicates that, similar to the SPR result, each of HMGB1A and TAT-HMGB1A binds to HMGB1. Furthermore, based on the result that only one band was observed in HMGB1+TAT-MT, it can be seen that TAT-HMGB1A and HMGB1A proteins specifically bind to HMGB1.

Example 8: Pancreatic Islet Transplantation in Type 1 Diabetes-Induced Nude Mice 8-1. Diabetic Model To artificially induce diabetes, streptozotocin was dissolved in 200 μl of a citric acid buffer at a ratio of 200 μg per kg of body weight of a nude mouse, and subsequently this solution was injected into the abdominal cavity. After one week, blood glucose was measured and mice exhibiting a blood glucose level exceeding 350 mg/dl for two consecutive days were used as a diabetic model.

8-2. Kidney Xenotransplantation of TAT-HMGB1A-Treated Pancreatic Islets

Diabetes-induced experimental animals were anesthetized with an anesthetic. The area around the left kidney position of a mouse was thoroughly wiped with alcohol cofton and then incised. After the kidney was carefully isolated, 200 and 400 cells of each of control pancreatic islets without any treatment and TAT-HMGB1A-treated pancreatic islets were transplanted into the left renal endothelial membrane using Hamilton syringes, respectively. After transplantation, the skin of the experimental animals was sutured. The animals were observed at an appropriate temperature until awakening from the anesthesia. Blood was drawn from the tail vein of the mice transplanted with pancreatic islets between 1 and 3 pm every other day, and blood glucose was measured using the One Touch Ultra Glucose Test Strip. Blood glucose was measured for 30 days after transplantation.

8-3. Evaluation of Reactivity Depending on Change in Blood Glucose Level by Intraperitoneal Glucose Tolerance Test (IPGTT) for Transplanted Nude Mice D-glucose was dissolved in PBS at a ratio of 200 mg/ml. Pancreatic islets-transplanted ICR-SCID mice were fasted for 6 hours. D-glucose dissolved in PBS was intraperitoneally injected at a ratio of 10 μl per g of mouse body weight. Blood samples were obtained from the tail veins of mice at 5, 10, 15, 20, 30, 60, 90 and 120 minutes, and blood glucose levels were measured using the One Touch Ultra Glucose Test Strip (Johnson & Johnson Lifescan Glucometer).

8-4. Tissue Examination for Pancreatic Islets Transplanted into Kidney 30 days after transplantation, mice were sacrificed to isolate the kidneys. The isolated kidneys were gently rinsed with PBS to remove blood and allowed to stand overnight in a 10% formaldehyde solution for fixation. Paraffin blocks for the fixed kidneys were prepared. The paraffin block was serially sectioned to a thickness of 5 μm, and then the location of the transplanted pancreatic islets was found using H&E staining. Among the serialized slides, slide samples around the slide number corresponding to a slide where pancreatic islets were present were subjected to an immunoassay for insulin, HMGB1 and 6× His tag.

Figure 8A:
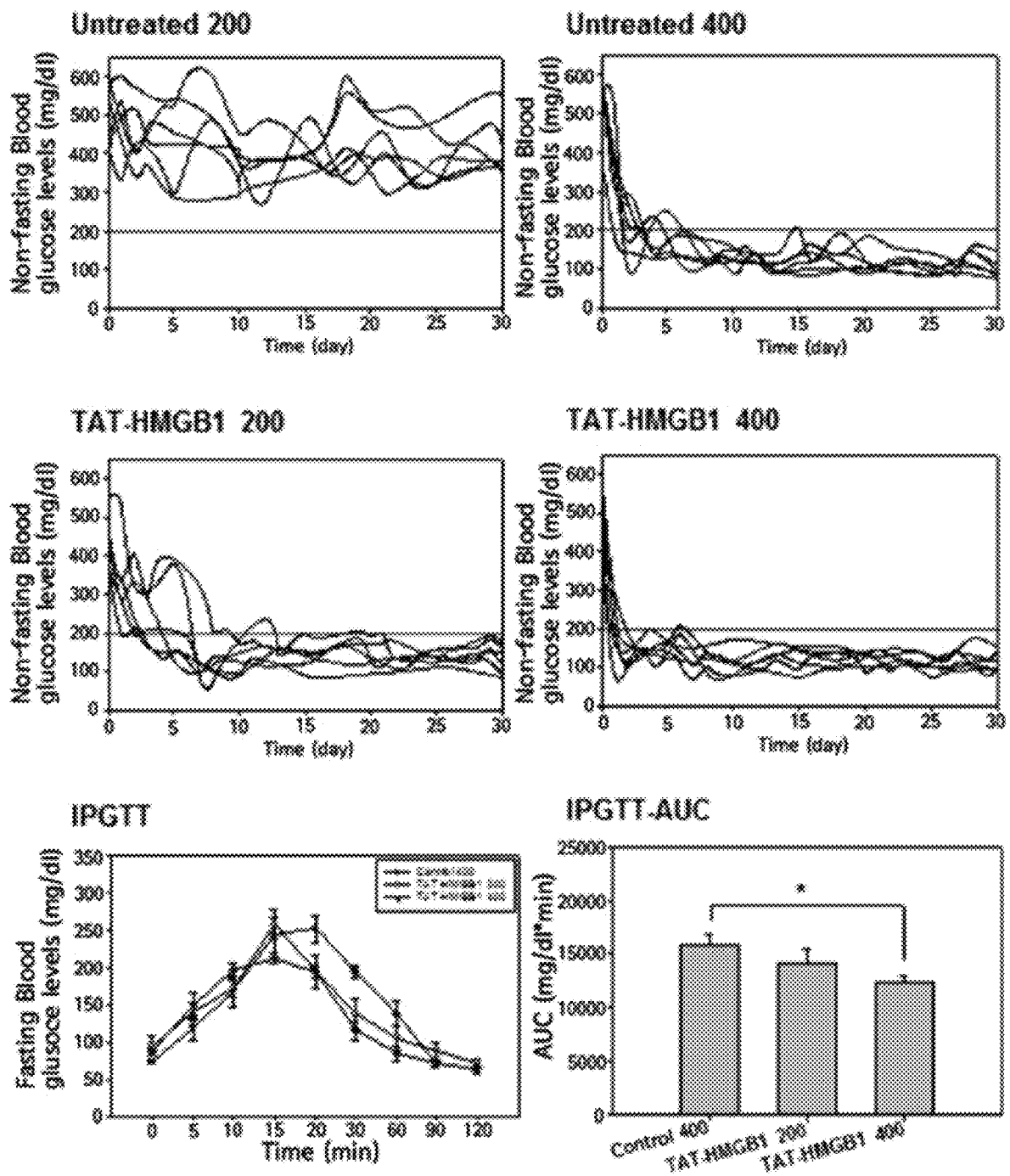
FIGS. 8A and 8B show normal blood glucose regulation capacity, the presence or absence of inflammation, insulin secretion capacity, and the amount of intracellularly-introduced samples depending on each sample treatment in type 1 diabetes-induced nude mice upon pancreatic islet transplantation.
Figure 8B:
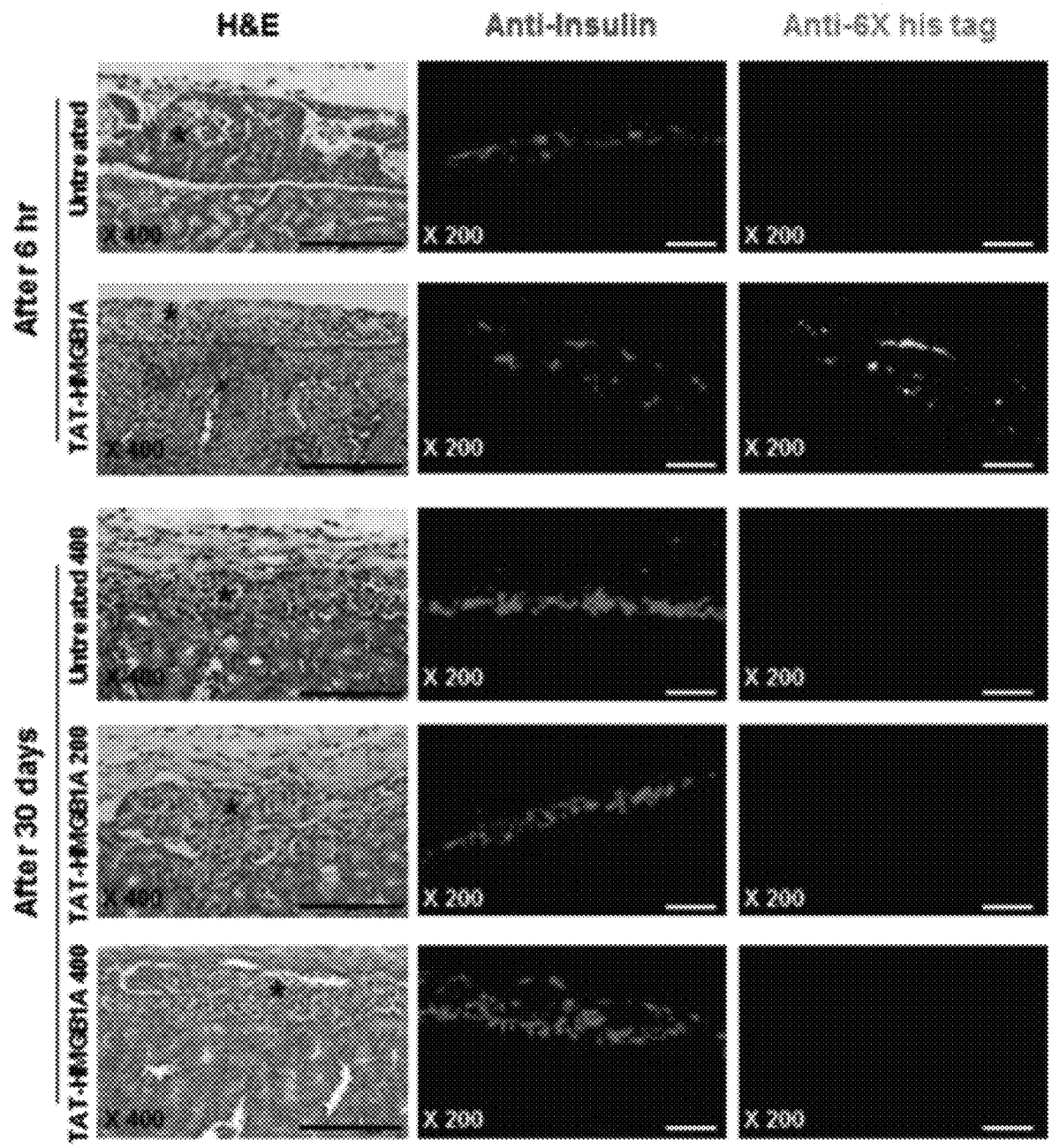

Nude mice are T-cell deficient mice, and immune responses do not occur significantly in the nude mice. Thus, nude mice can be used as an animal model suitable for evaluating the efficacy of basic cell transplantation. Generally, when pancreatic islet cells isolated from rats are transplanted into mice in a diabetic model, the number of transplanted cells capable of normalizing glucose levels is about 400. After inducing type 1 diabetes by STZ, 200 and 400 cells of each of control pancreatic islets without any treatment (untreated) and TAT-HMGB1A-treated pancreatic islets were transplanted into the left renal endothelial membrane, respectively. In the control group (untreated pancreatic islet cells), 200 cells were not sufficient to normalize blood glucose levels, whereas in the case of TAT-HMGB1A-treated pancreatic islet cells, blood glucose levels were recovered normally when 200 cells were transplanted (see FIG. 8). In the control group transplanted with untreated pancreatic islet cells, most of transplanted pancreatic islet cells failed to function due to inflammatory responses triggered by surgical injury, whereas in the group transplanted with TAT-HMGB1A-treated pancreatic islet cells, transplanted pancreatic islet cells functioned. These results can be explained by the fact that TAT-HMGB1A reduces the action of HMGB1, which is released due to surgical injury, to some extent. In addition, when IPGTT was performed 30 days after transplantation, the group transplanted with 200 TAT-HMGB1A-treated pancreatic islet cells and the group transplanted with 400 TAT-HMGB1A-treated pancreatic islet cells exhibited similar results in normalizing in vivo glucose levels (see FIG. 8). In addition, after transplantation, TAT-HMGB1A-treated pancreatic islet cells steadily secreted insulin at an early time point (6 hours after transplantation) and at a late time point (30 days after transplantation). According to the result of 6× His tag staining, which allows the estimation of the amount of TAT-HMGB1A proteins in TAT-HMGB1A-treated pancreatic islet cells, TAT-HMGB1A proteins were observed in the early stage of transplantation but not observed after 30 days. However, since HMGB1-induced inflammation after transplantation was maximized 6 hours after transplantation, it was considered that these results were not significant.

Example 9: Pancreatic Islet Transplantation in Type 1 Diabetes-Induced BALB/c Mice 9-1. Diabetic Model To artificially induce diabetes, streptozotocin was dissolved in 200 μl of a citric acid buffer at a ratio of 200 mg per kg of body weight of a BALB/c mouse, and subsequently this solution was injected into the abdominal cavity. After one week, blood glucose was measured and mice exhibiting a blood glucose level exceeding 350 mg/dl for two consecutive days were used as a diabetic model.

9-2. Kidney Xenotransplantation of TAT-HMGB1A-Treated Pancreatic Islets

Diabetes-induced experimental animals were anesthetized with an anesthetic. The area around the left kidney position of a mouse was thoroughly wiped with alcohol cotton and then incised. After the kidney was carefully isolated, 400 cells of each of control pancreatic islets without any treatment and TAT-HMGB1A-treated pancreatic islets were transplanted into the left renal endothelial membrane using Hamilton Syringes. After transplantation, the skin of the experimental animals was sutured. The animals were observed at an appropriate temperature until awakening from the anesthesia. Blood was drawn from the tail vein of the mice transplanted with pancreatic islets between 1 and 3 pm every day, and blood glucose was measured using One Touch Ultra Glucose Test Strip (Johnson & Johnson Lifescan Glucometer). From the day following transplantation, the organs of mice exhibiting a blood glucose level exceeding 350 mg/dl for three consecutive days were extracted.

9-3. Tissue Xxamination for Pancreatic Islets Transplanted in Kidney

After transplantation, mice were sacrificed at 6 hours and 3 days after failure of normal blood glucose control, and the kidneys were treated with a fixing solution. Paraffin blocks for the fixed kidneys were prepared, and H&E staining and immunostaining for insulin, 6× His tag and HMGB1 were carried out.

TABLE 2

|  | Number of days of survival | Median ± S.E. |
|---|---|---|
| Untreated (n = 8) | 3, 5, 6, 5, 6, 7, 8, 7 | 6 ± 0.54 |
| TAT-HMGB1A (n = 8) | 12, 8, 3, 13, 12, 9, 10, 13 | 11 ± 1.19 |

Figure 9:
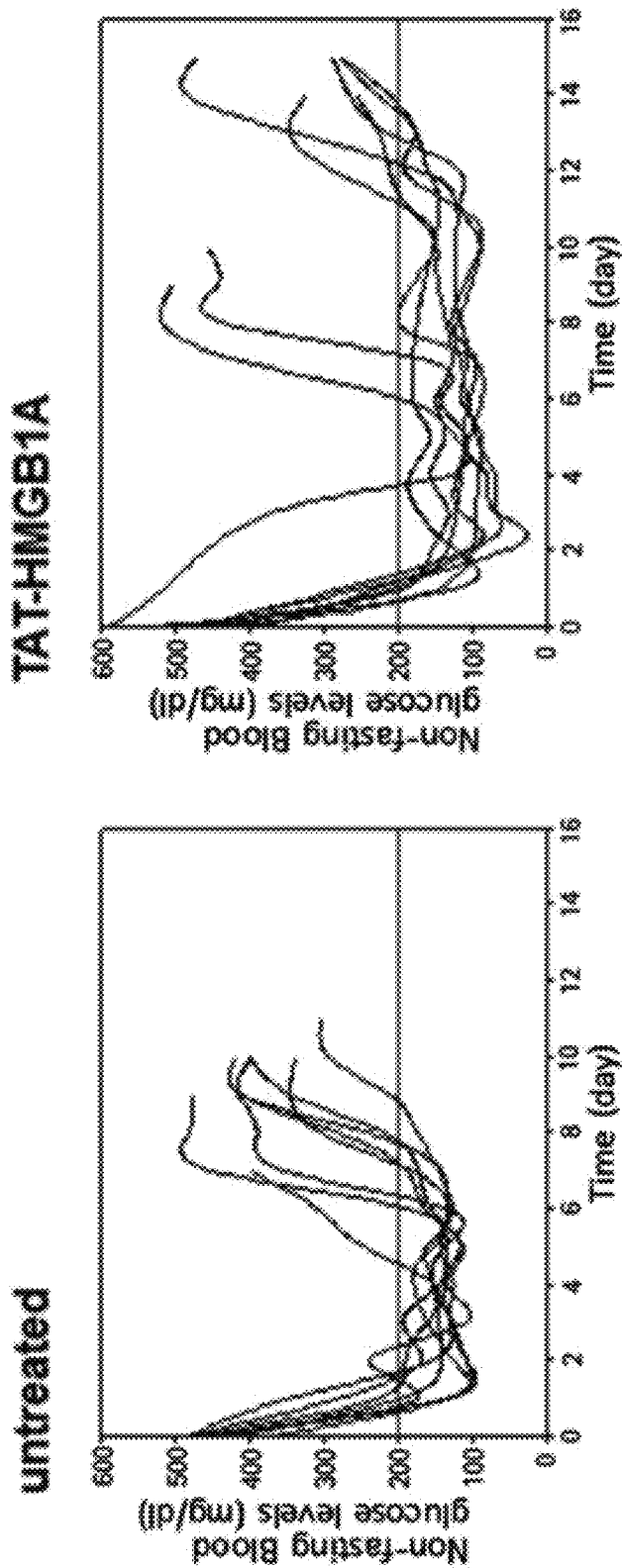
FIG. 9 shows the survival period of transplanted pancreatic islet cells in type 1 diabetes-induced B ALB/c mice upon pancreatic islet transplantation.
Figure 10:
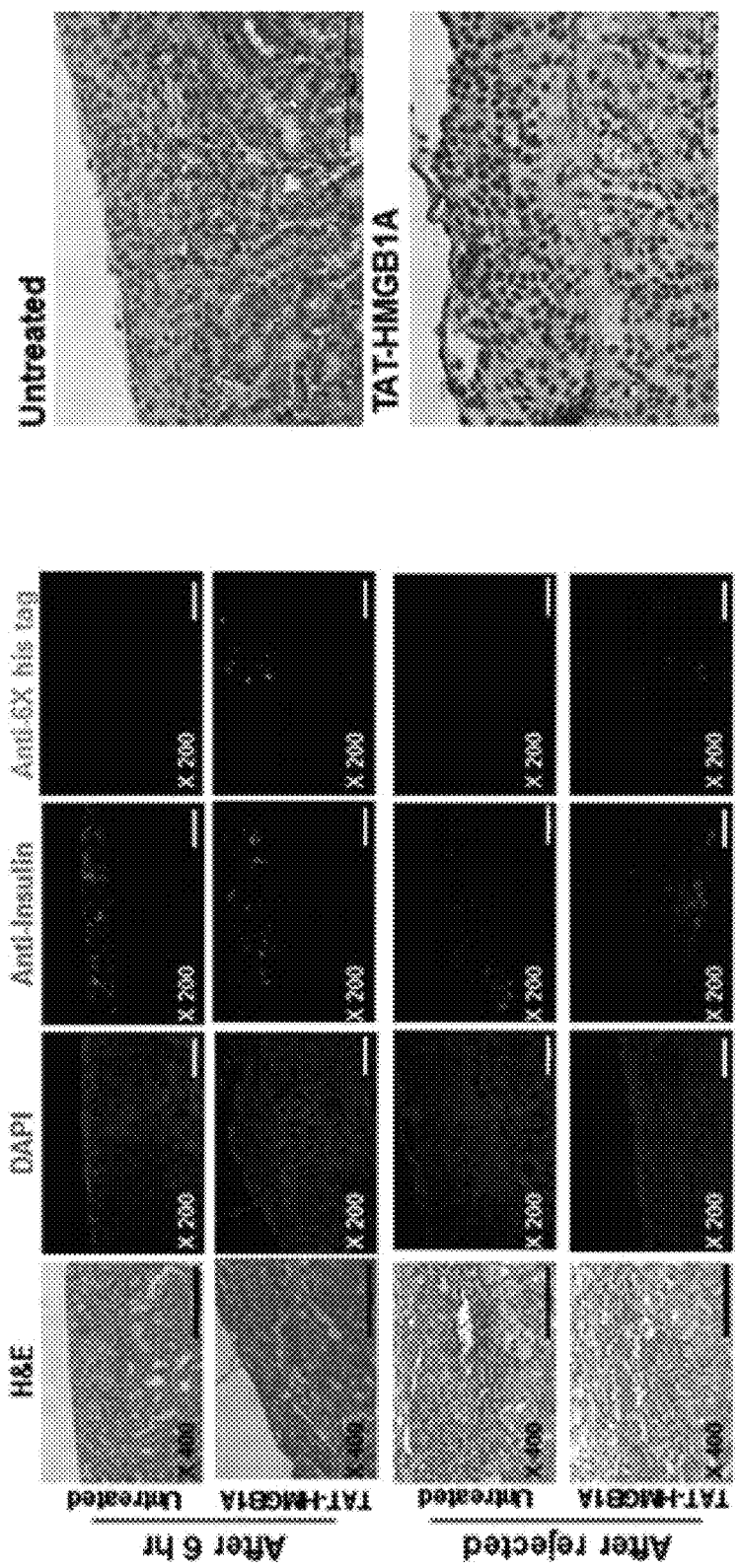
FIG. 10 shows the results of H&E staining and staining of insulin, 6× His tag and HMGB1 for pancreatic islets transplanted into the kidney of type 1 diabetes-induced BALB/c mice upon pancreatic islet transplantation.

BALB/c mice are animals whose immune responses are normal, unlike nude mice. When pancreatic islet cells isolated from rats are transplanted into BALB/c mice, apoptosis occurs in most of transplanted pancreatic islet cells due to severe inflammatory responses and immune responses, and thus it is difficult for normal glucose control to last beyond a week. In addition, using BALB/c mice, we can determine to what extent TAT-HMGB1A can reduce the action of HMGB1 produced by immune responses following pancreatic islet cell transplantation. As shown in Table 2 and FIG. 9, when TAT-HMGB1A-treated pancreatic islet cells and control pancreatic islet cells were transplanted into the left renal membranes of BALB/c mice, the viability of TAT-HMGB1A-treated pancreatic islet cells was about two-fold higher than that of control pancreatic islet cells. In addition, at 6 hours after transplantation, in the case of control pancreatic islet cells, HMGB1 was highly stained around the transplanted cells and in the cytoplasms of the transplanted cells, whereas in the case of TAT-HMGB1A-treated pancreatic islet cells, HMGB1 staining was observed in the nuclei of the transplanted cells (see FIG. 10). These results indicate that TAT-HMGB1A can reduce inflammatory responses mediated by HMGB1 produced after transplantation.

Example 10

Identification of TAT-HMGB1A Delivery into Pancreatic Cancer Cells other than Pancreatic Islet Cells
10-1. Measurement of Viability of TAT-HMGB1A in Pancreatic Cancer Cells
MIA PaCa-2, a pancreatic cell line, was inoculated into a 96 well plate at $1 \times 10^4$ cells/well and treated with TAT-HMGB1A at 0, 5, 10, 15 and 20 µM, respectively, and then incubated for 24 hours. Thereafter, cell viability was measured using CCK-8.
10-2. Measurement of Effect of TAT-HMGB1A on Proliferation of Pancreatic Cancer Cells
MIA PaCa-2 cells were inoculated into a 96 well plate at $5 \times 10^3$ cells/well and treated with 10 µM TAT-HMGB1A. Cell proliferation was measured at days 1, 4 and 7 after treatment.
10-3. Identification of TAT-HMGB1A Delivery into Pancreatic Cancer Cells
Pancreatic cancer cells were treated with 10 µM Alexa 488 fluorescent dye-conjugated TAT-HMGB1A and incubated for 24 hours. After incubation, the cells were washed with PBS, and fluorescence images were taken. To determine the efficiency of TAT-HMGB1A delivery, TAT-HMGB1A delivered into pancreatic cancer cells was measured using flow cytometry.

Figure 11A:
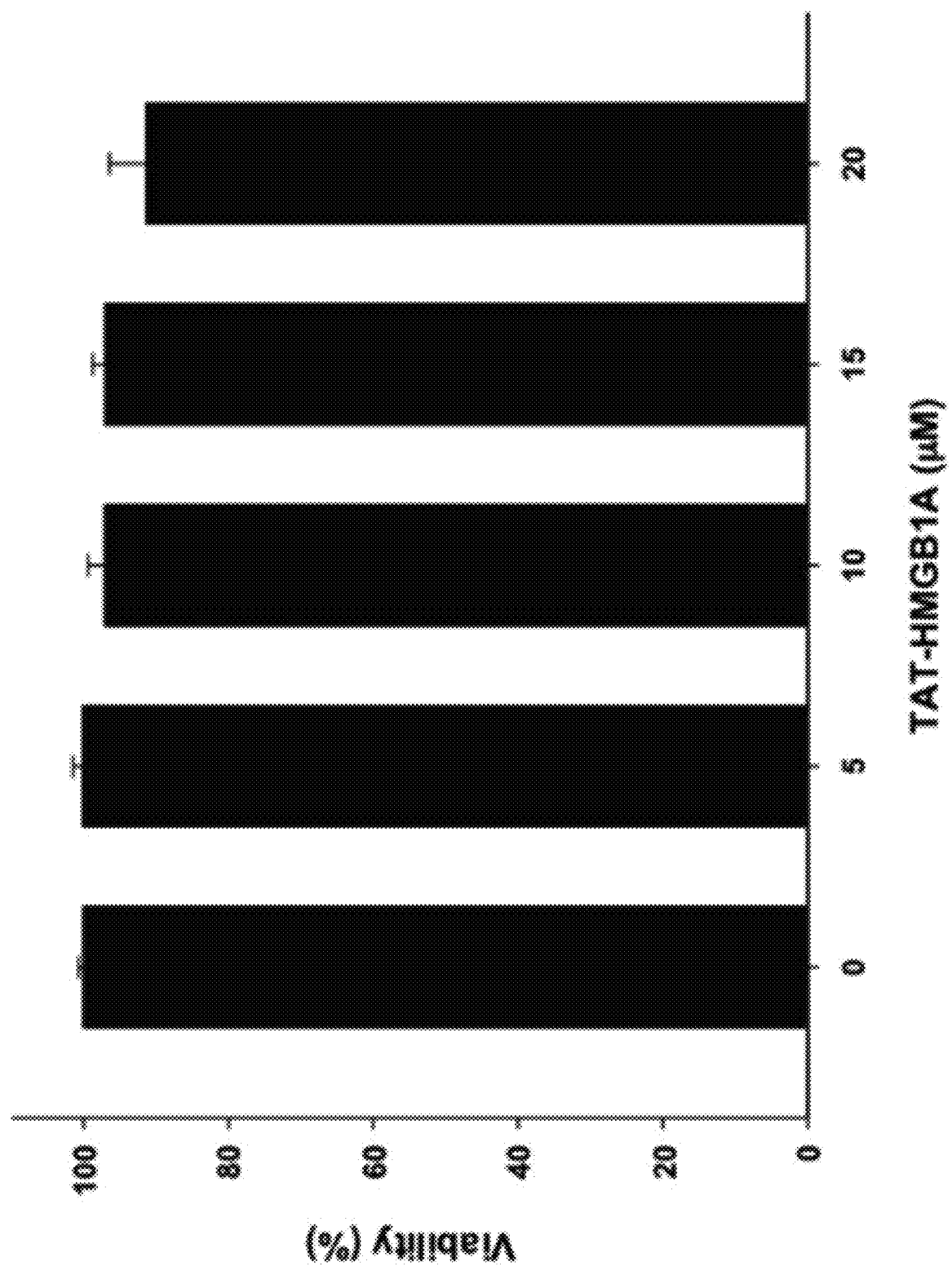
FIGS. 11A to 11C shows the results of confirming the delivery of TAT-HMGB1A into cancer cells.
Figure 11B:
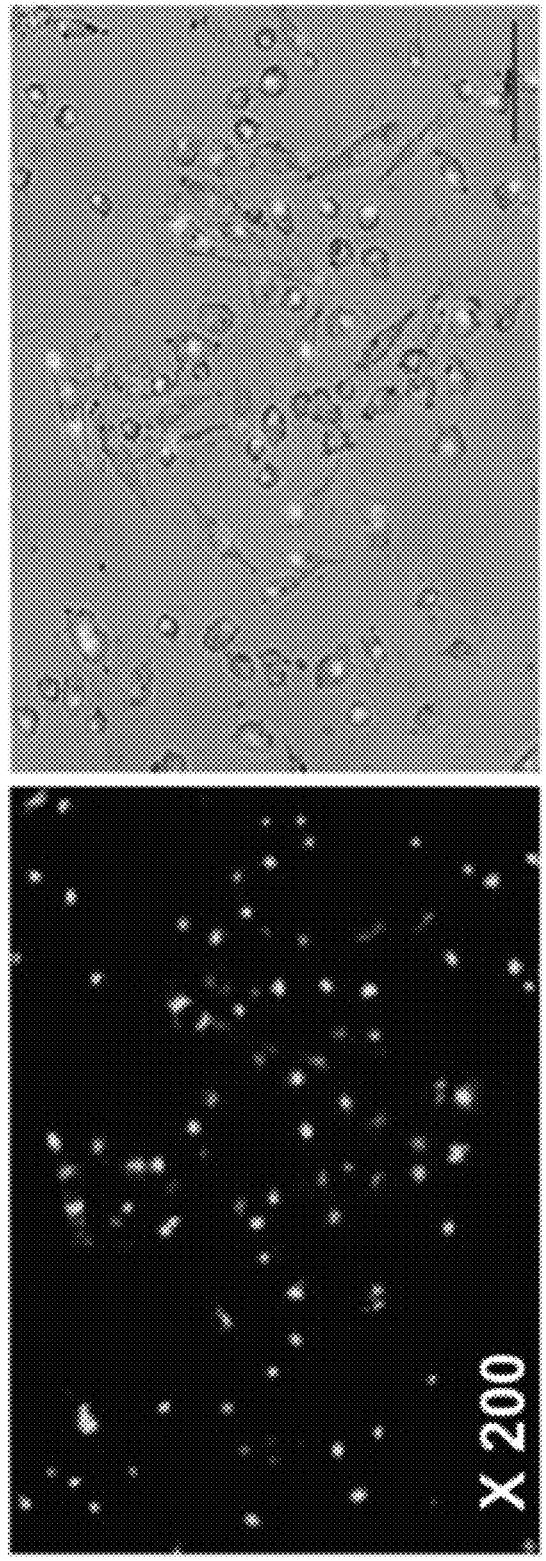
Figure 11C:
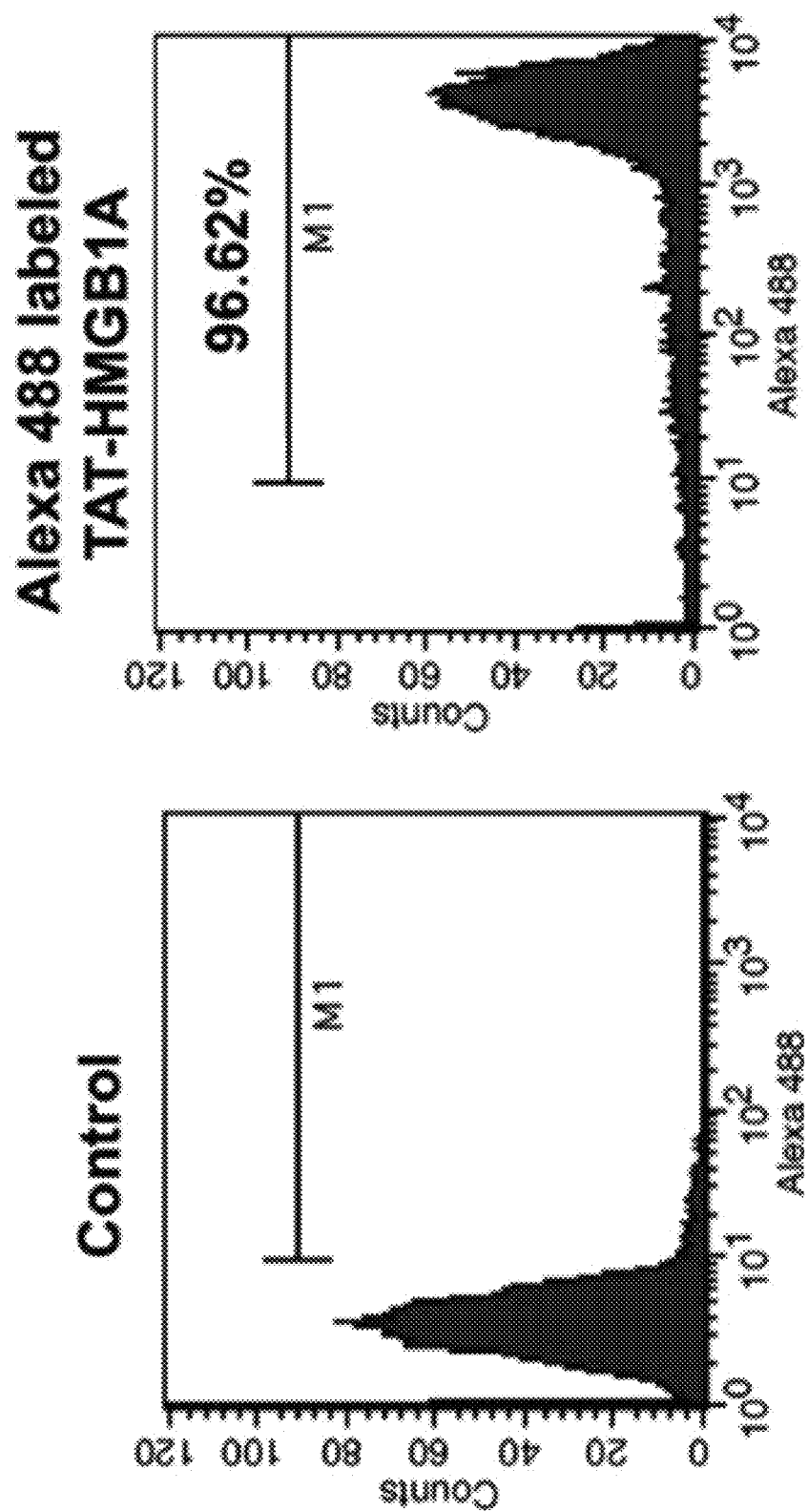

MIA PaCa-2 cells, a typical pancreatic cancer cell line, contain a large amount of HMGB1. First, in order to investigate whether the delivery of TAT-HMGB1A is toxic to pancreatic cancer cells, pancreatic cancer cells were treated with TAT-HMGB1A at different concentrations. As shown in FIG. 11A, no toxicity was observed at any concentration of TAT-HMGB1A. In addition, when cell proliferation was measured after cells were persistently exposed to 10 µM TAT-HMGB1A, the treated cells exhibited a proliferation rate similar to untreated cells. To investigate whether TAT-HMGB1A is efficiently delivered into pancreatic cancer cells, pancreatic cancer cells were treated with Alexa 488 green-fluorescent dye-conjugated TAT-HMGB1A at the same concentration. As a result, most of cells exhibited green fluorescence, indicating that TAT-HMGB1A was efficiently delivered into pancreatic cancer cells (see FIG. 11B). As a result of measurement of delivery efficiency using flow cytometry, more than 95% of the proteins were delivered into pancreatic cancer cells, which is quite high (see FIG. 11C).

Example 11: Measurement of Amount of HMGB1 Remaining in Pancreatic Cancer Cells Under Hypoxic Conditions The effect of TAT-HMGB1A treatment on pancreatic cancer cells was determined under HMGB1 secretion conditions. MIA PaCa-2 cells not treated with TAT-HMGB1A were prepared as a control group, and MIA PaCa-2 cells pretreated with 10 µM TAT-HMGB1A for 24 hours were prepared. The prepared cells were placed in a hypoxia chamber and incubated for 6 hours under hypoxic conditions (1% $O_2$, 5% $CO_2$ and 94% $N_2$). After incubation, the cells were lysed and subjected to western blotting.

Figure 12:
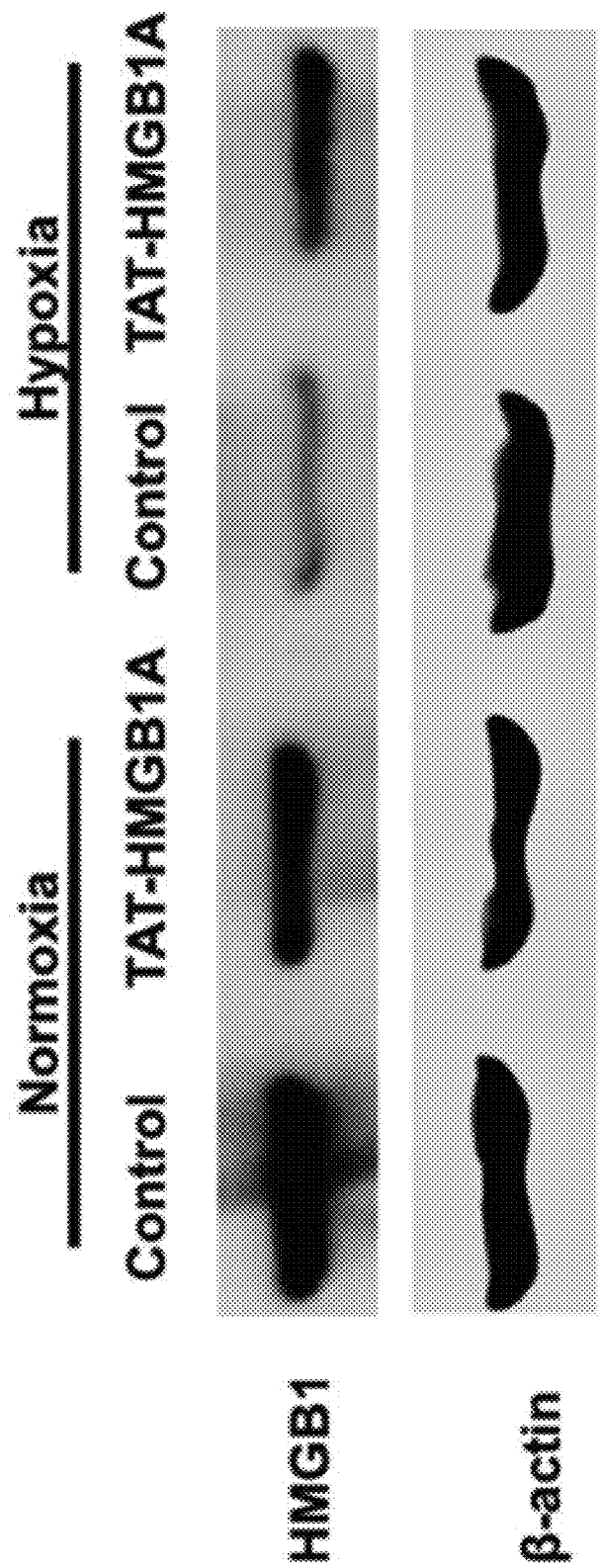
FIG. 12 shows the inhibitory effect of TAT-HMGB1A on HMGB1 release when cancer cells were treated with TAT-HMGB1A under HMGB1 release conditions.

Cancer cells are exposed to hypoxic conditions during their growth, and this hypoxic condition causes cell necrosis and promotes secretion of HMGB1 in the cells. In order to measure this phenomenon, MIA. PaCa-2 cells treated with TAT-HMGB1A and MIA PaCa-2 cells not treated with TAT-HMGB1A were incubated under hypoxic conditions for 6 hours, and the amount of residual HMGB1 was compared using western blotting. The two groups did not exhibit no difference in the amount of HMGB1 under normoxic conditions. However, when cells are exposed to hypoxic conditions for an extended period of time, cell necrosis occurs and HMGB1 is continuously secreted from the cells and moves to the surrounding environment of the cells. It was confirmed that in pancreatic cancer cells treated with TAT-HMGB1A, TAT-HMGB1A delivered into the cells binds to HMGB1, which is secreted from the cells, and inhibits the secretion of HMGB1. This result was confirmed by western blot analysis (see FIG. 12).

Example 12: Effect of TAT-HMGB1A on HUVECs, Other Cells 12-1. Measurement of Cell Viability by TAT-HMGB1A
Human umbilical vein endothelial cells (HUVECs) (LONZA, Korea) were inoculated into a 96 well plate at $4 \times 10^4$ cells/well and treated with TAT-HMGB1A at 0, 5, 10, 15, 20 and 25 µM, respectively, and then incubated for 24 hours. Thereafter, cell viability was measured using CCK-8.
12-2. Identification of TAT-HMGB1A Delivery into HUVECs
HINECs were treated with 10 µM Alexa 488 fluorescent dye-conjugated TAT-HMGB1A and incubated for 24 hours. After incubation, the cells were washed with PBS, and the fluorescent signals were observed using a fluorescence microscope.

Figure 13A:
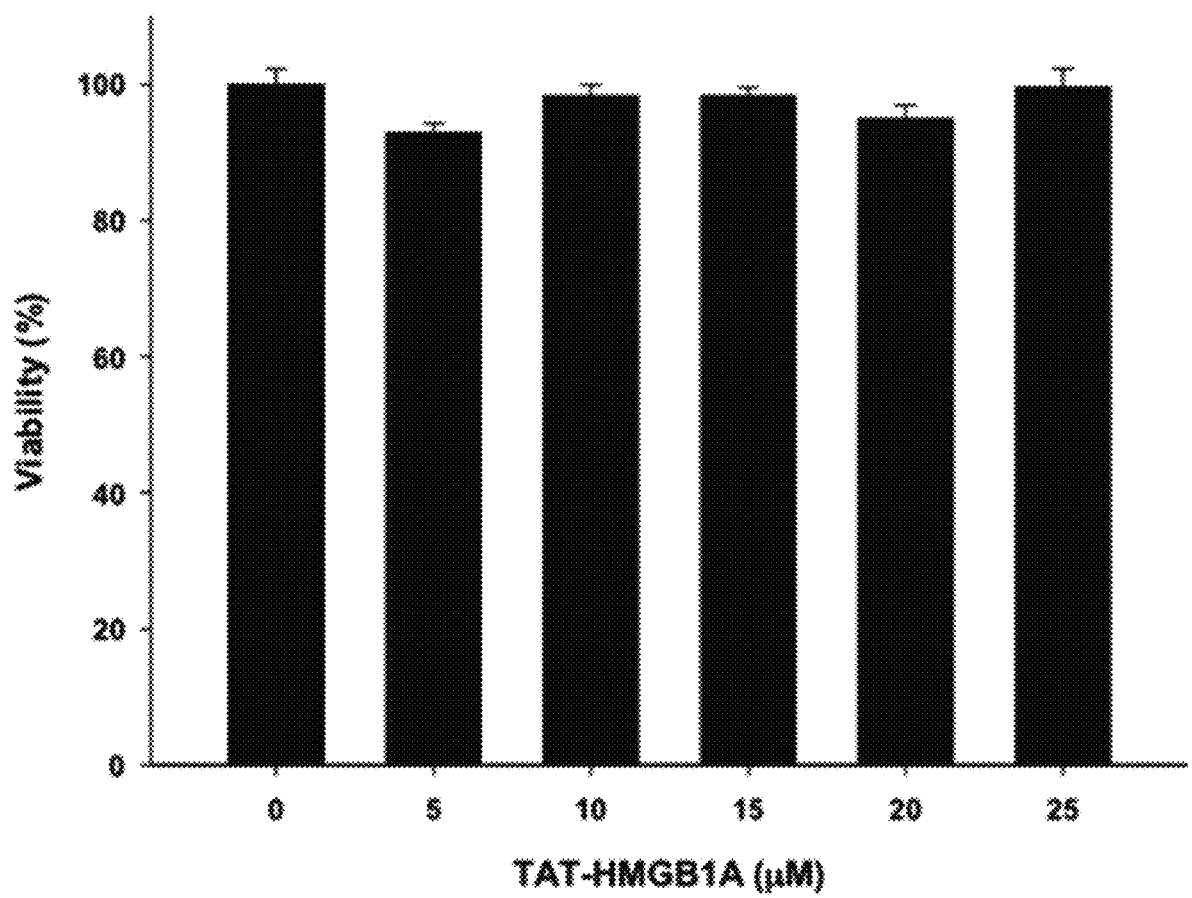
FIGS. 13A to 13C are results showing the viability of human umbilical vein endothelial cells (HUVECs) by TAT-HMGB1A and the intracellular delivery of TAT-HMGB1A.
Figure 13B:
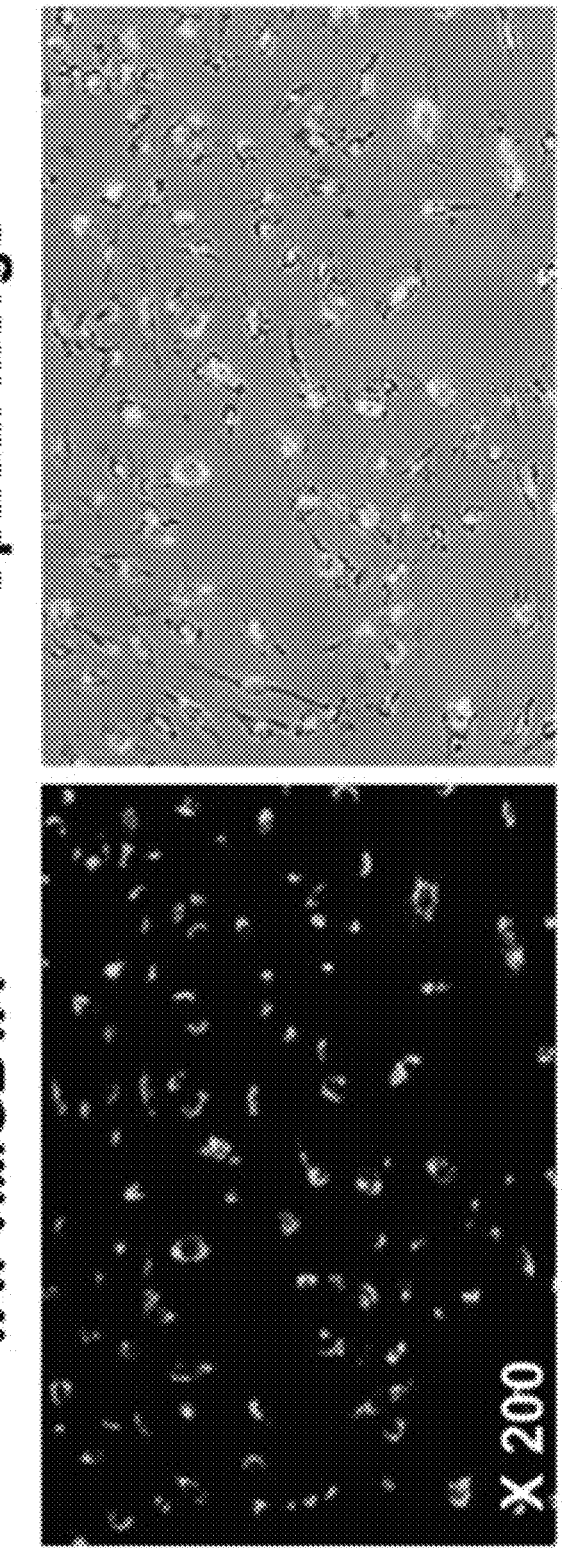
Figure 13C:
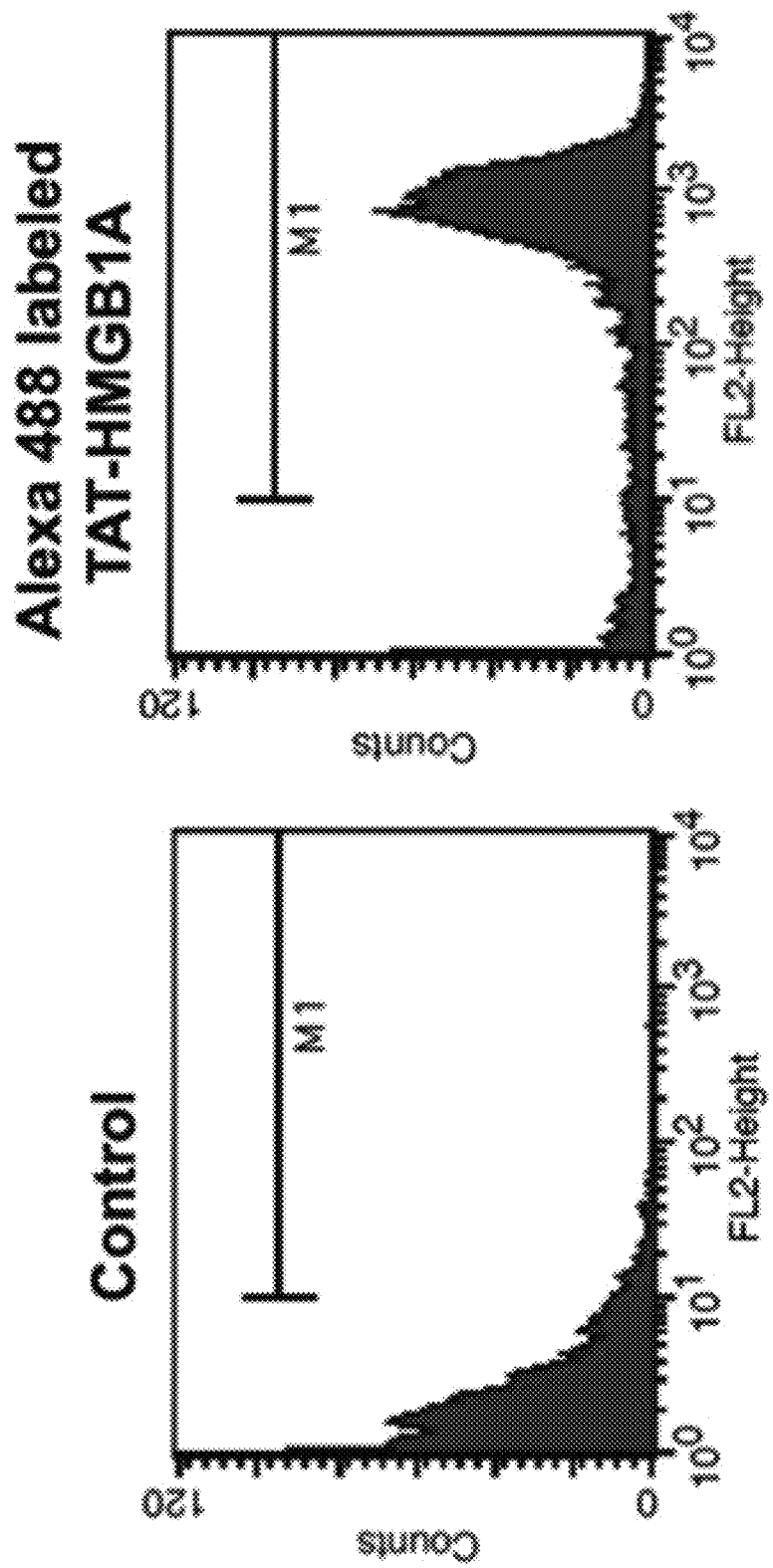

When HUVECs were treated with TAT-HMGB1A at different concentrations, no toxicity was observed at any concentration of TAT-HMGB1A (see FIG. 13A). In addition, when HUVECs were treated with Alexa 488 dye-conjugated TAT-HMGB1A, Alexa 488 fluorescent signals were observed in the cells, indicating that TAT-HMGB1A can be delivered into HUVECs (see FIG. 13B). As a result of measurement of delivery efficiency using flow cytometry, 95% or more of the proteins were delivered into HUVECs, which is quite high (see FIG. 13C).

Example 13: Analysis of Cell Infiltration

For Matrigel coating, 0.2 mg/ml Matrigel was added into inserts (8 μm pore) and incubated for 24 hours. HUVECs were diluted to a number of $4 \times 10^5$ in a serum free medium and aliquoted into each insert. The bottoms of wells were filled with serum free media containing each of VEGF (20 ng/ml), HMGB1 (500 ng/ml) and HMGB1 (500 ng/ml)+TAT-HMGB-1A (10 μM). The inserts were put into wells, the bottoms of which were filled with the conditioned media (bottom solution), and incubated for 24 hours. After washing the inserts, cells in the inserts were fixed using 4% paraformaldehyde, and stained using a crystal violet dye for 30 minutes. After removing non-infiltrating cells, images were taken. Thereafter, the crystal violet dye stained in the cells was dissolved by methanol, and absorbance was measured at 540 nm.

Figure 14:
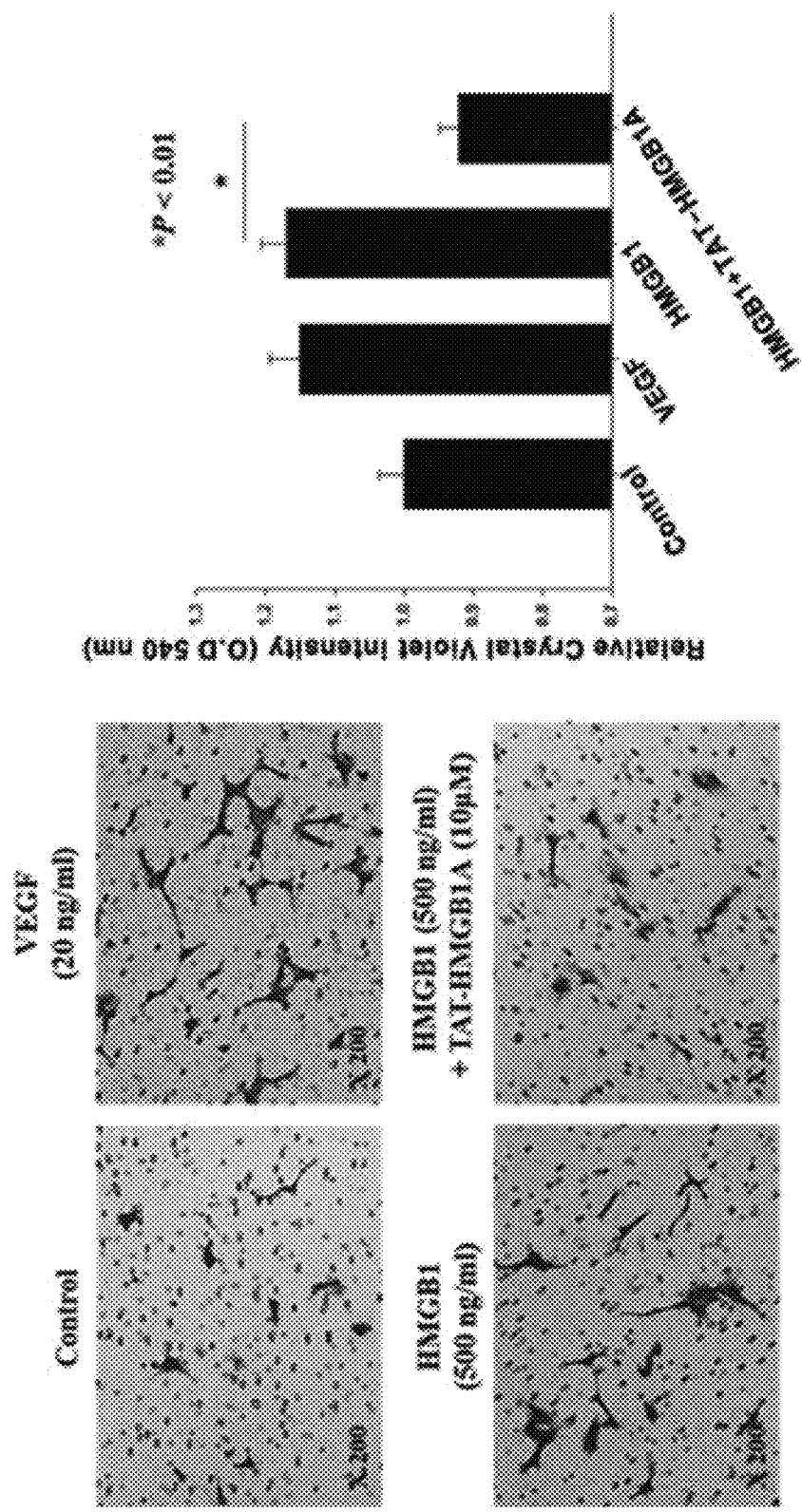
FIG. 14 shows the results of a cell infiltration analysis using HUVECs.

VEGF is typically used to activate HUVECs and has been used as a positive control in the present invention. When HUVECs were stimulated with 500 ng/ml HMGB1, cell infiltration was observed similar to that of VEGF stimulation. However, when HUVECs were co-treated with HMGB1 and TAT-HMGB1A, the degree of cell infiltration was reduced due the inhibitory effect of TAT-HMGB1A on HMGB1 (see FIG. 14). These results imply that TAT-HMGB1A acts as a competitive antagonist for HMGB1.

Example 14: Analysis of Rat Aortic Ring

120 μl of Matrigel (reduced form) was added into each well of a 48 well plate and gelated. Aortic rings extracted from SD-rats were inserted in the Matrigel-containing wells of the 48 well plate. 100 μl of Matrigel was further added and gelated. Serum free media containing each of no additive, HMGB1 (500 ng/ml) and HMGB1 (500 ng/ml) TAT-HMGB1A (10 μl) were added to each well, followed by observation for 6 days.

Figure 15A:
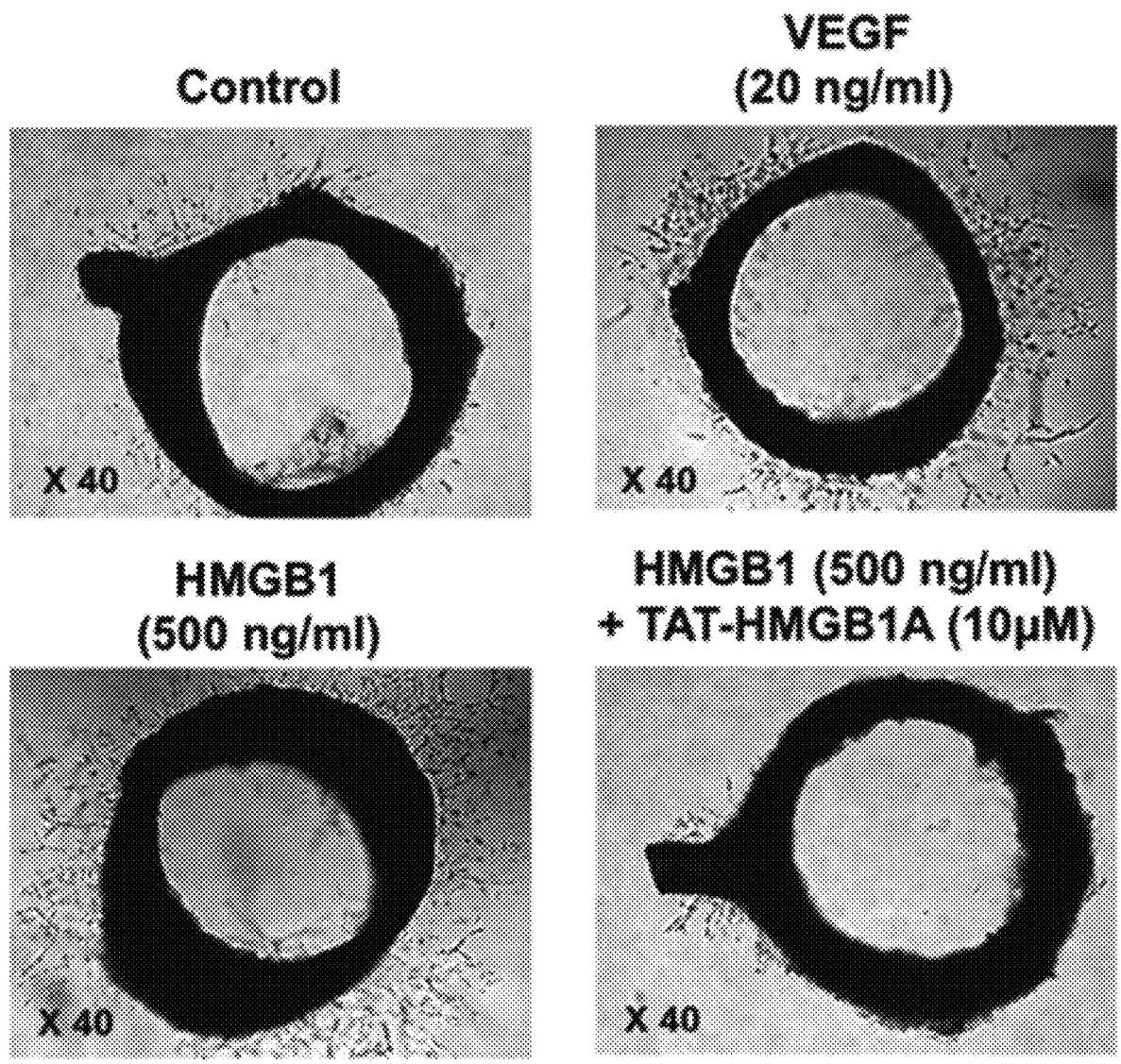
FIGS. 15A and 15B are results showing the inhibitory effect of TAT-HMGB1A on angiogenesis using aortic rings of rats.
Figure 15B:
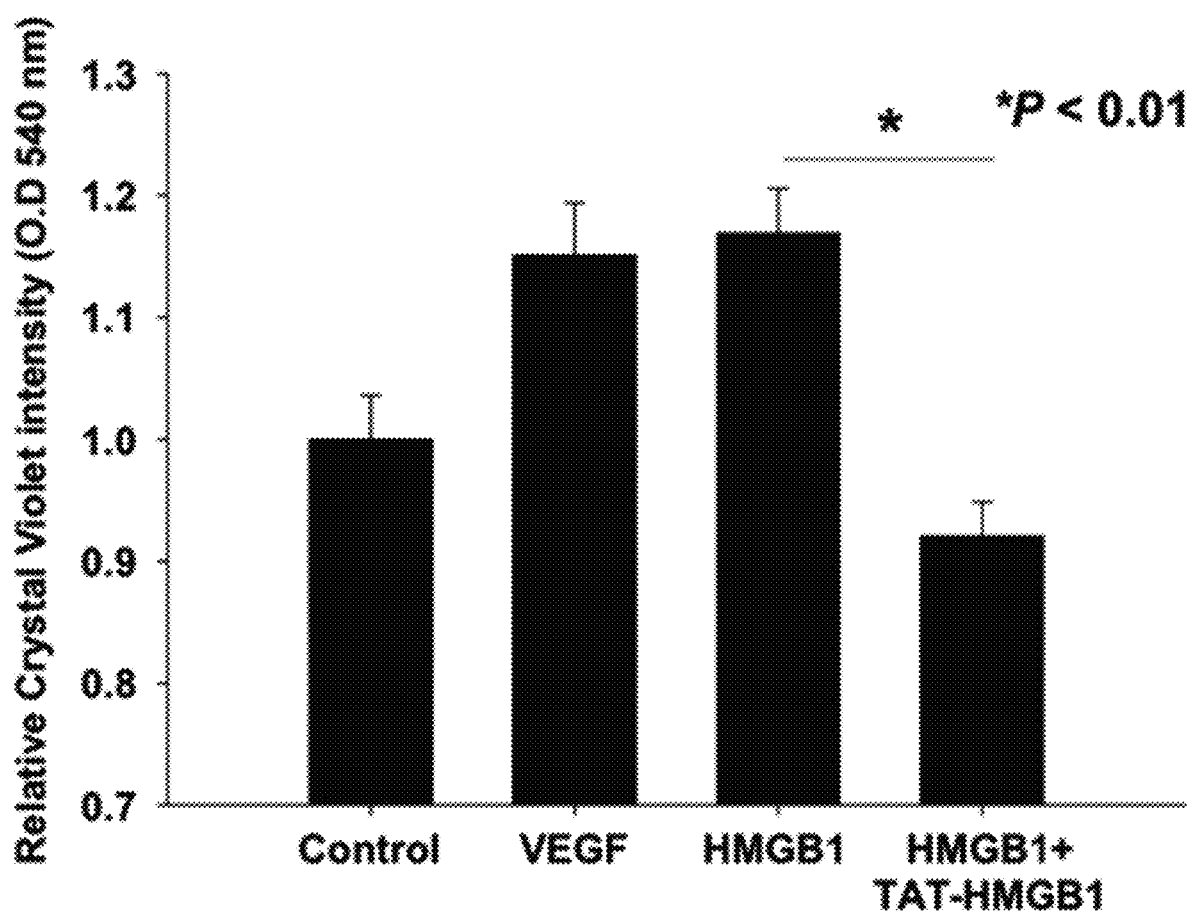

As a result of rat aortic ring analysis, microvascular formation around the aortic ring was more frequent with treatment of 500 ng/ml) HMGB1 (see FIG. 15A). This result suggests that HMGB1 facilitates microvascular formation and HMGB1 plays an important role in angiogenesis. In addition, simultaneous treatment of HMGB1 and TAT-HMGB1A reduced microvascular formation. As a result of quantifying the above data, the HMGB1-treated group exhibited about a three-fold increase in microvascular formation compared to the control group and the group co-treated with HMGB1 and TAT-HMGB1A, and this is statistically valid (see FIG. 15B).

Example 15: Change of HMGB1 Expression in HUVECs Depending on HMGB1 Treatment For serum starvation, HUVECs were cultured in a serum free medium for 6 hours. 10 μM TAT-HMGB1A was added to HUVECs treated with 500 ng/ml HMGB1 for 24 hours and incubated for 24 hours. After cell lysis, western blotting was performed using HMGB1 antibodies.

Figure 16:
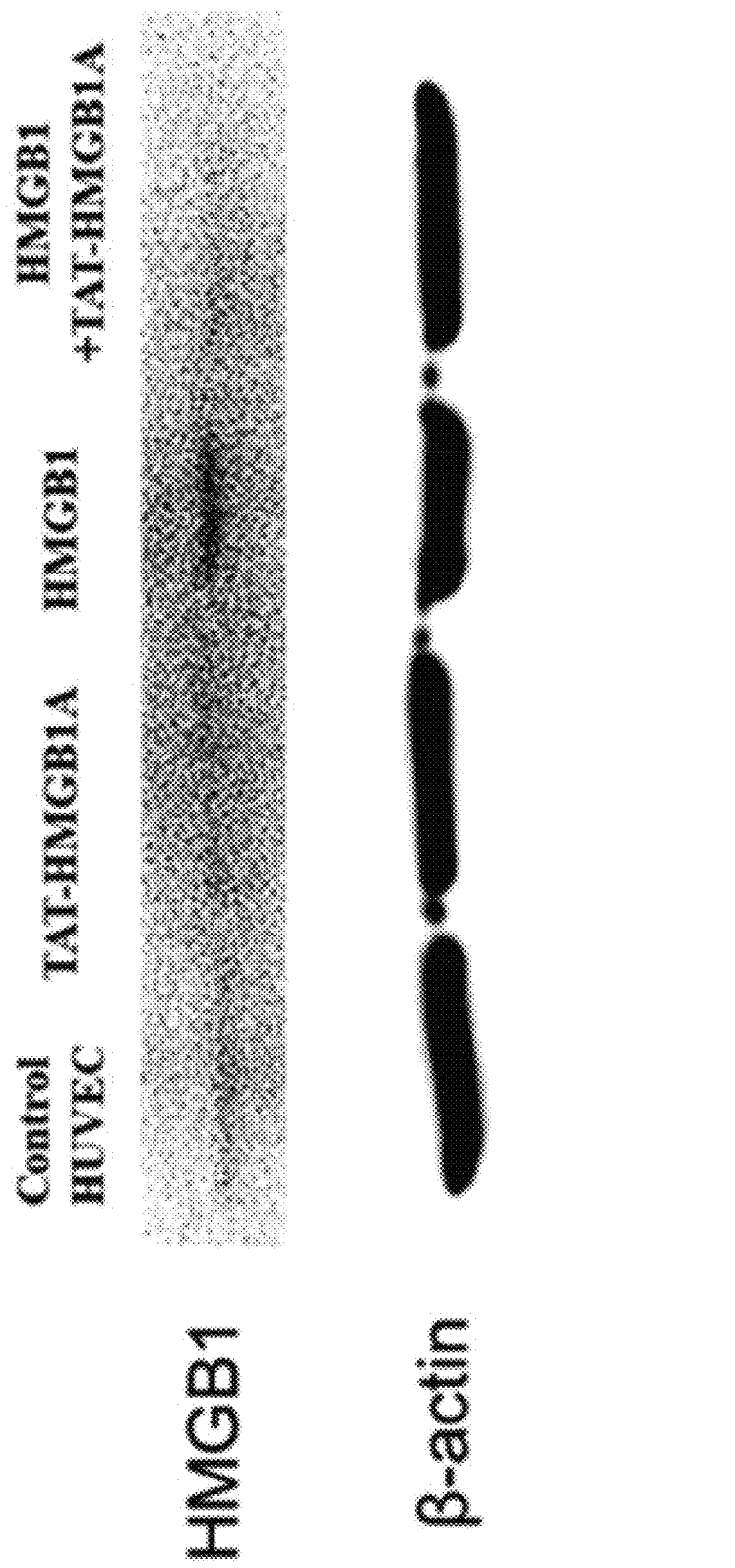
FIG. 16 is a result showing change in HMGB1 expression within HUVECs depending on HMGB1A treatment.

When HUVECs were subjected to starvation in a serum free medium for 6 hours, the expression of HMGB1 is silenced and the amount of HMGB1 expression is significantly reduced. However, when HMGB1 was treated at a concentration of 500 ng/ml, the expression of endogenous HMGB1 in HUVECs was increased by HMGB1 stimulation. This phenomenon was confirmed by the increased thickness of the band corresponding to HMGB1 in western blotting. However, when HMGB1-treated cells were further treated with TAT-HMGB1A, the expression of endogenous HMGB1 was reduced, showing a level similar to that of the control group (see FIG. 16). These results indicate that TAT-HMGB1A inhibits the release of intracellular HMGB1 into the extracellular environment, while TAT-HMGB1A inhibits the expression of HMGB1 stimulated by exogenous HMGB1. Based on these results, it is expected that cells having RAGE or TLR4, an HMGB1 receptor, will exhibit the same results. In the case of pancreatic islet cells, since the cells have HMGB1 receptors, the same results can be obtained.

The present invention has been described in detail. It will be apparent to those skilled in the art that such specific description is only a preferred embodiment and that the scope of the present invention is not limited thereto. Accordingly, the actual scope of the present invention will be defined by the appended claims and their equivalents.

---

The invention claimed is:

1. A method of inhibiting rejection of transplanted cells comprising a step of pretreating cells prior to transplantation with a pharmaceutical composition comprising a high mobility group box 1 A domain (HMGB1A) combined with a protein transduction domain (PTD) as an active ingredient.

2. The method of claim 1, wherein the PTD is selected from the group consisting of trans-acting activator of transcription (Tat), penetratin, transportan, Virus Protein 22 (VP-22), amphipathic peptides, Pep-1 peptide, model amphipathic peptide (MAP), sweet arrow peptide (SAP), cationic peptides, oligoarginine, human calcitonin fragment 9-32 (hCT(9-32)) and Vascular-Endothelial-Cadherin-derived cell-penetrating peptide (pVEC).

3. The method of claim 2, wherein the PTD is Tat.

4. The method of claim 1, wherein the cells are pancreatic islet cells, adult stem cells, embryonic stem cells or induced pluripotent stem cells (IPSCs).

5. The method of claim 1, wherein the cell transplantation is for treatment of diseases selected from the group consisting of type 1 diabetes, type 2 diabetes, diabetic chronic kidney diseases, leukemia, aplastic anemia, Huntington's disease, stroke, spinal cord injuries and multiple sclerosis.

6. The method of claim 5, wherein the cell transplantation is for treatment of type 1 diabetes.

* * * * *